(12) United States Patent
Merkel et al.

(10) Patent No.: US 11,884,976 B2
(45) Date of Patent: Jan. 30, 2024

(54) RESIN COMPOSITION AND FLOW CELLS INCORPORATING THE SAME

(71) Applicants: ILLUMINA, INC., San Diego, CA (US); ILLUMINA CAMBRIDGE LIMITED, Cambridge (GB)

(72) Inventors: Timothy J. Merkel, San Diego, CA (US); Wayne N. George, London (GB); Andrew A. Brown, Cambridge (GB); Audrey Zak, San Diego, CA (US); Gianluca Andrea Artioli, Cambridge (GB); Julia Morrison, Grays (GB); Nikolai Romanov, Cambridge (GB); Lorenzo Berti, San Diego, CA (US); Graham Boud, San Diego, CA (US)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 818 days.

(21) Appl. No.: 16/515,790

(22) Filed: Jul. 18, 2019

(65) Prior Publication Data
US 2020/0024661 A1   Jan. 23, 2020

Related U.S. Application Data

(60) Provisional application No. 62/701,228, filed on Jul. 20, 2018.

(51) Int. Cl.
*C12Q 1/6874* (2018.01)
*C08G 77/442* (2006.01)
(Continued)

(52) U.S. Cl.
CPC ......... *C12Q 1/6874* (2013.01); *C08G 77/442* (2013.01); *C08L 33/04* (2013.01);
(Continued)

(58) Field of Classification Search
CPC ........ C08F 22/10; C08F 30/08; C08F 130/08; C08F 230/08; C08G 77/20;
(Continued)

(56) References Cited

U.S. PATENT DOCUMENTS 5,054,872 A * 10/1991 Fan .................. G02B 1/045
385/130
8,033,663 B2 * 10/2011 Valeri .................. G02B 1/14
522/170

(Continued)

FOREIGN PATENT DOCUMENTS

EP   1794655   12/2011
EP   2717097   4/2014
(Continued)

OTHER PUBLICATIONS

Scifinder properties of CAS No. 75980-60-8 (2021).*
(Continued)

*Primary Examiner* — Kregg T Brooks
(74) *Attorney, Agent, or Firm* — Dierker & Kavanaugh, P.C.

(57) ABSTRACT

An example of a resin composition includes a free radical curable resin matrix including an acrylate and a siloxane, and a free radical photoinitiator. When cured, the resin composition has low or no autofluorescence when exposed to blue excitation wavelengths ranging from about 380 nm to about 480 nm or green excitation wavelengths ranging from about 510 nm to about 560 nm.

9 Claims, 5 Drawing Sheets

(51) Int. Cl.
- *C09D 153/00* (2006.01)
- *C12Q 1/6876* (2018.01)
- *C09D 163/00* (2006.01)
- *C08L 63/00* (2006.01)
- *C08L 33/04* (2006.01)

(52) U.S. Cl.
CPC ............ *C08L 63/00* (2013.01); *C09D 153/00* (2013.01); *C09D 163/00* (2013.01); *C12Q 1/6876* (2013.01)

(58) Field of Classification Search
CPC ... C08G 2261/522; C08L 33/04; C08L 35/02; C08L 63/00–10
See application file for complete search history.

(56) References Cited

U.S. PATENT DOCUMENTS

| | | | |
|---|---|---|---|
| 2003/0225199 A1* | 12/2003 | Breunig | G03F 7/0755 524/588 |
| 2003/0235787 A1* | 12/2003 | Watts | B82Y 40/00 525/178 |
| 2004/0163570 A1* | 8/2004 | Vanmaele | C09D 11/101 106/31.13 |
| 2005/0260522 A1 | 11/2005 | Weber et al. | |
| 2007/0224084 A1* | 9/2007 | Holmes | A61B 5/150022 422/50 |
| 2010/0014121 A1 | 1/2010 | Hyuga et al. | |
| 2010/0141211 A1 | 6/2010 | Yazami | |
| 2013/0040854 A1* | 2/2013 | Ramasubramanian | G01N 33/56961 506/10 |
| 2016/0025637 A1 | 1/2016 | Halverson et al. | |
| 2016/0136873 A1 | 5/2016 | Chouiki | |
| 2016/0137839 A1 | 5/2016 | Rolland et al. | |
| 2016/0251469 A1 | 9/2016 | Kobayashi et al. | |
| 2016/0331261 A1 | 11/2016 | Someya et al. | |
| 2017/0204290 A1 | 7/2017 | Simoff et al. | |
| 2019/0135983 A1 | 5/2019 | Maliverney et al. | |

FOREIGN PATENT DOCUMENTS

| | | | | |
|---|---|---|---|---|
| JP | 2000044857 A | * | 2/2000 | ............ C09D 11/34 |
| JP | 2012183530 A | | 9/2012 | |
| JP | 2015096559 A | | 5/2015 | |
| JP | 2017057270 A | * | 3/2017 | |
| JP | 2018058944 A | * | 4/2018 | |
| RU | 2603639 C1 | | 11/2016 | |
| RU | 2627867 C1 | | 8/2017 | |
| WO | WO-2007079070 A1 | * | 7/2007 | ............ A61K 6/30 |
| WO | 2013129565 A1 | | 9/2013 | |
| WO | 2014/054763 A1 | | 4/2014 | |
| WO | 2015064310 A1 | | 5/2015 | |
| WO | 2015119197 A1 | | 8/2015 | |
| WO | WO-2016018918 A1 | * | 2/2016 | ............ B05D 3/067 |
| WO | 2017007753 A1 | | 1/2017 | |
| WO | 2017187030 A1 | | 11/2017 | |

OTHER PUBLICATIONS

Partial machine translation of JP-2017057270-A (2017).*
Partial machine translation of JP-2018058944-A (2018).*
Gelest, UMS-992 (Acryloxpropyl)methylsiloxane Homopolymer MSDS (2015).*
Partial machine translation of JP-2000044857-A (2000).*
Pai, et al., "A Photoresist with Low Fluorescence for Bioanalytical Applications", Anal Chem. Nov. 15, 2007; 79(22); 8774-8780.
Decrop, D., et al., "Single-Step Imprinting of Femtoliter Microwell Arrays Allows Digital Bioassays with Attomolar Limit of Detection", ACS Applied Materials & Interfaces, Mar. 7, 2017, 10418-10426.
Kehagias, et al., "Stamp replication for thermal and UV nanoprint lithography using a UV-sensitive silsequioxane resist", Microelectronic Engineering 86, 2009, 776-778.
Bernhard, David, D., et al., "Fabrication and Characterization of Microwell Array Chemical Sensors", Analytical Chemistry, American Chemical Society, US, vol. 73, No. 11, pp. 2484-2490, Jun. 1, 2001.
Cheng, Chao-Min, et al., "Maskless fabrication of small-scale structures through controlling phase interactions", Applied Physics A, Materials Science & Processing, Springer, Berlin, DE, vol. 102, No. 1, pp. 185-188, Dec. 2, 2010.

* cited by examiner

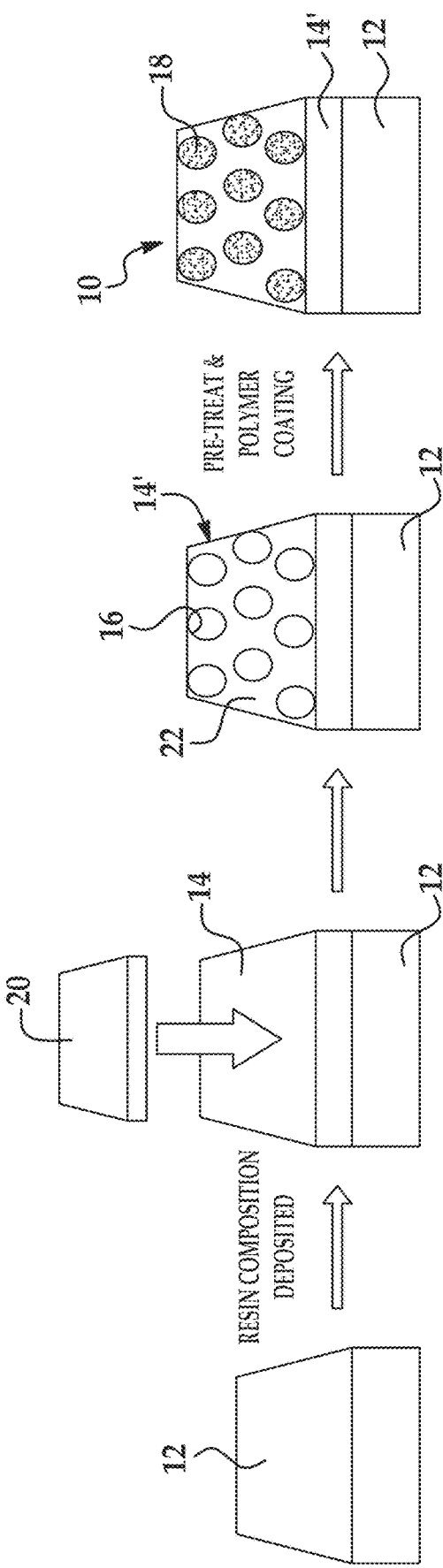

RESIN COMPOSITION AND FLOW CELLS INCORPORATING THE SAME

CROSS-REFERENCE TO RELATED APPLICATIONS

This application claims the benefit of U.S. Provisional Application Ser. No. 62/701,228, filed Jul. 20, 2018, the content of which is incorporated by reference herein in its entirety.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes in humans and other organisms. In certain applications, for example, individual DNA and RNA probes may be attached at small locations in a geometric grid (or randomly) on an array support. A test sample, e.g., from a known person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

INTRODUCTION

In an aspect, a resin composition comprise a free radical curable resin matrix including an acrylate and a siloxane; and a free radical photoinitiator; wherein, when cured, the resin composition has low or no autofluorescence when exposed to blue excitation wavelengths ranging from about 380 nm to about 480 nm or green excitation wavelengths ranging from about 510 nm to about 560 nm.

In an example, the cured resin composition has low autofluorescence, wherein the low autofluorescence corresponds with a grey value of less than 25,000 when the cured resin composition is exposed to the blue excitation wavelengths.

In another example, the cured resin composition has low autofluorescence, wherein the low autofluorescence corresponds with a grey value of less than 5,000 when the cured resin composition is exposed to the blue excitation wavelengths.

In still another example, the cured resin composition has low autofluorescence, wherein the low autofluorescence corresponds with a grey value of less than 10,000 when the cured resin composition is exposed to the green excitation wavelengths.

In yet a further example, the cured resin composition has low autofluorescence, wherein the low autofluorescence corresponds with a grey value of less than 2,500 when the cured resin composition is exposed to the green excitation wavelengths.

In an example, the free radical curable resin matrix comprises an acrylate selected from the group consisting of 1,3-bis(3-methacryloxypropyl) tetramethyldisiloxane, methacryloxypropyl-terminated polydimethylsiloxane, tetramethyl tetrakis[3-acryloxypropyl]cyclotetrasiloxane, methacryl polyhedral oligomeric silsesquioxane, acrylo polyhedral oligomeric silsesquioxane, acryloxypropyl methylsiloxane homopolymer, and combinations thereof.

In an example, the free radical photoinitiator is 2-ethyl-9,10-dimethoxyanthracene.

In another example, the free radical photoinitiator is selected from the group consisting of 2,2-dimethoxy-2-phenylacetophenone and 2-ethoxy-2-phenylacetophenone.

In still another example, the free radical photoinitiator is a phosphine oxide, wherein the phosphine oxide is selected from the group consisting of diphenyl(2,4,6-trimethylbenzoyl)phosphine oxide, a blend of diphenyl(2,4,6-trimethylbenzoyl)phosphine oxide and 2-hydroxy-2-methylpropiophenone, phenylbis(2,4,6-,trimethylbenzoyl)phosphine oxide, ethyl(2,4,6-trimethylbenzoyl)phenylphosphinate, and combinations thereof.

In an example, the resin composition further comprises a dark quencher or an electron acceptor.

In an example, a weight % ratio of the free radical curable resin matrix to the free radical photoinitiator ranges from about 99.8:0.2 to about 90:10.

In an example, the resin composition further comprises an epoxy resin matrix; and a photoacid generator.

It is to be understood that any features of this aspect of the resin composition may be combined together in any desirable manner and/or configuration to achieve the benefits as described in this disclosure, including for example the relatively low autofluorescence.

In another aspect, a flow cell comprises a substrate; and a cured, patterned resin on the substrate, the cured, patterned resin including depressions separated by interstitial regions, and the cured, patterned resin having been formed from a resin composition including: a free radical curable resin matrix including an acrylate and a siloxane; and a free radical photoinitiator; wherein the cured, patterned resin has low or no autofluorescence when exposed to blue excitation wavelengths ranging from about 380 nm to about 480 nm or green excitation wavelengths ranging from about 510 nm to about 560 nm.

In an example, the flow cell further comprises a polymer coating in the depressions; and a primer grafted to the polymer coating.

In an example, the cured, patterned resin has low autofluorescence, wherein the low autofluorescence corresponds with a grey value of less than 25,000 when the cured, patterned resin is exposed to the blue excitation wavelengths.

In another example, the cured, patterned resin has low autofluorescence, wherein the low autofluorescence corresponds with a grey value of less than 10,000 when the cured, patterned resin is exposed to the green excitation wavelengths.

In yet another example, the resin composition further includes an epoxy resin matrix; and a photoacid generator.

In an example, the free radical curable resin matrix comprises an acrylate selected from the group consisting of 1,3-bis(3-methacryloxypropyl) tetramethyldisiloxane, methacryloxypropyl-terminated polydimethylsiloxane, tetramethyl tetrakis[3-acryloxypropyl]cyclotetrasiloxane, methacryl polyhedral oligomeric silsesquioxane, acrylo polyhedral oligomeric silsesquioxane, acryloxypropyl methylsiloxane homopolymer, and combinations thereof.

In an example, the free radical photoinitiator is selected from the group consisting of 2-ethyl-9,10-dimethoxyanthracene, 2,2-dimethoxy-2-phenylacetophenone, and 2-ethoxy-2-phenylacetophenone.

In another example, the free radical photoinitiator is a phosphine oxide selected from the group consisting of diphenyl(2,4,6-trimethylbenzoyl)phosphine oxide, a blend of diphenyl(2,4,6-trimethylbenzoyl)phosphine oxide and 2-hydroxy-2-methylpropiophenone, phenylbis(2,4,6-,trimethylbenzoyl)phosphine oxide, ethyl(2,4,6-trimethylbenzoyl)phenylphosphinate, and combinations thereof.

In an example, the resin composition further comprises a dark quencher or an electron acceptor.

In an example, a weight % ratio of the free radical curable resin matrix to the free radical photoinitiator in the resin composition ranges from about 99.8:0.2 to about 90:10.

It is to be understood that any features of this aspect of the flow cell may be combined together in any desirable manner to achieve the benefits as described in this disclosure, including for example the relatively low autofluorescence. Moreover, it is to be understood that any combination of features of this aspect of the flow cell and/or of the resin composition may be used together, and/or that any features from either or both of these aspects may be combined with any of the examples disclosed herein to achieve the benefits as described in this disclosure, including for example the relatively low autofluorescence.

In still another aspect, a method comprises depositing a resin composition on a substrate, the resin composition including: a free radical curable resin matrix including an acrylate and a siloxane; and a free radical photoinitiator; nanoimprinting the deposited resin composition using a working stamp; and curing the deposited resin composition to form a cured, patterned resin; wherein the cured, patterned resin has low or no autofluorescence when exposed to blue excitation wavelengths ranging from about 380 nm to about 480 nm or green excitation wavelengths ranging from about 510 nm to about 560 nm.

It is to be understood that any features of this aspect of the method may be combined together in any desirable manner to achieve the benefits as described in this disclosure, including for example the relatively low autofluorescence. Moreover, it is to be understood that any combination of features from the method and/or from the flow cell and/or from the resin composition may be used together, and/or that any features from any or all of these aspects may be combined with any of the features of the examples disclosed herein to achieve the benefits as described in this disclosure, including for example the relatively low autofluorescence.

Still further, it is to be understood that any features of any of the method and/or of the flow cell and/or of the resin composition may be combined together in any desirable manner, and/or may be combined with any of the examples disclosed herein to achieve the benefits as described in this disclosure, including for example the relatively low autofluorescence.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 2A through 2E are schematic perspective views which together depict an example of the method disclosed herein;

FIG. 2F is a schematic and cross-sectional view taken along line 2F-2F of FIG. 2E;

DETAILED DESCRIPTION

Figure 1:
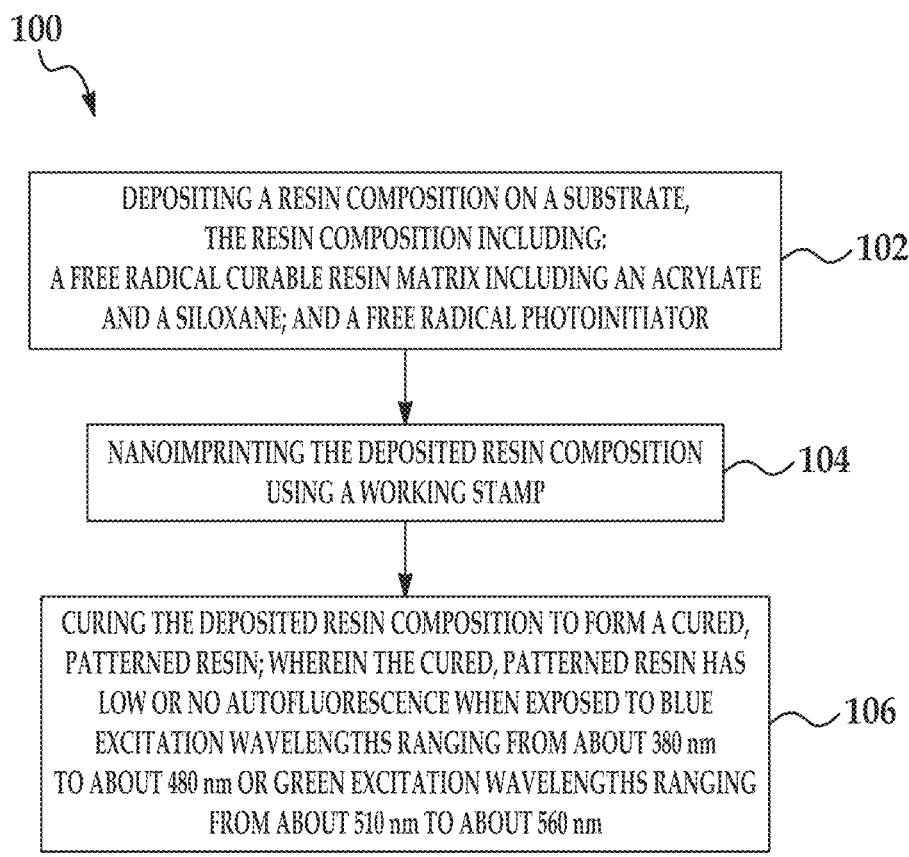
FIG. 1 is a flow diagram illustrating an example of a method disclosed herein.
Figure 3A:
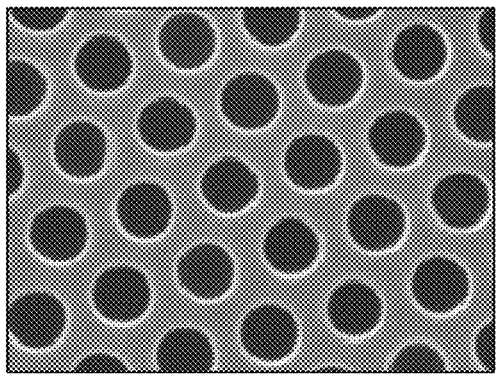
FIGS. 3A through 3F are scanning electron micrograph images of example wells formed using different examples of the resin compositions disclosed herein.
Figure 3B:
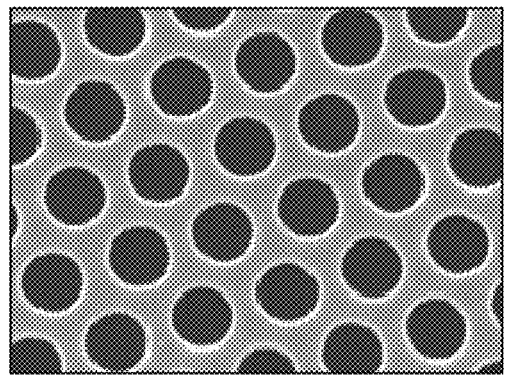
Figure 3C:
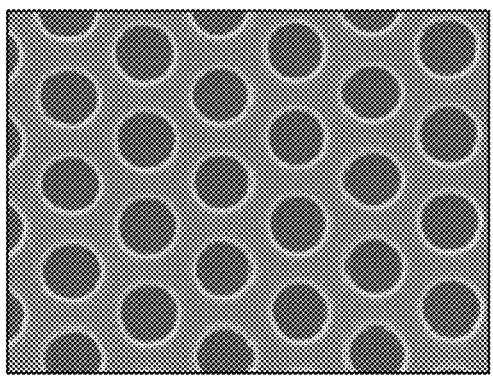
Figure 3D:
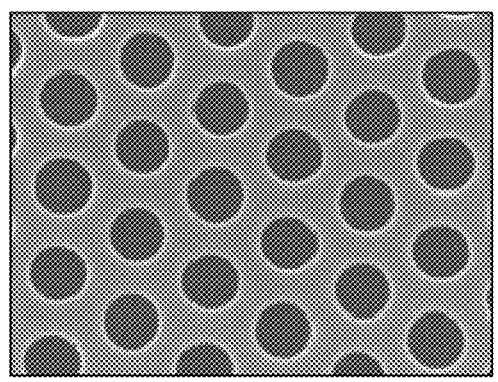
Figure 3E:
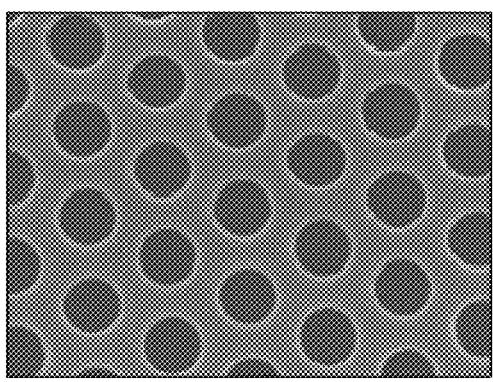
Figure 3F:
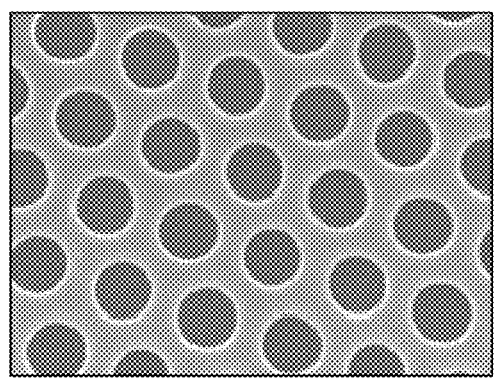

It is desirable for patterned flow cells used in sequencing applications to have basal levels of autofluorescence that enable signal to noise ratios (SNRs) that are high enough so that signals from individual clusters can be resolved during sequencing. Resin compositions used in patterned flow cells often include photoinitiators (e.g., free radical and/or cationic generators) to initiate curing during patterning of the composition. In theory, when the photoinitiators used have no absorption in the visible region, no fluorescence should occur when excited by the blue, green and/or red light sources used during sequencing. However, based on solution measurements of some free radical and cationic photoinitiator combinations, it has been found that undesirable autofluorescence may occur at excitation wavelengths of interest, even when little or no absorbance is predicted to occur based on the spectral properties of the resin components in the visible region.

The resin matrix of the resin composition disclosed herein is acrylate based (e.g., the resin includes an acrylate and/or a methacrylate) and exhibits relatively low levels of fluorescence after curing. Moreover, the acrylate based resin cures solely through a free radical mechanism. With this curing mechanism, a free radical photoinitiator can be used without other types of photoinitiators, such as cationic photoinitiators. This, in turn, can minimize, and in some instances even eliminate, intramolecular interactions that may otherwise occur between the different types photoinitiators (e.g., between some free radical and cationic photoinitiator combinations). It is believed that these intramolecular interactions may occur before or during ultraviolet (UV) light exposure, indicating that the energy exchange between the combination of photoinitiators and the subsequent formation of excited state complexes (exciplexes) and adducts may be contributing to the undesirable autofluorescence. It is further believed that because the resin composition disclosed herein does not experience the aforementioned intramolecular interactions, the cured resin composition disclosed herein can exhibit autofluorescence (when exposed to excitation wavelengths of interest (e.g., blue and/or green excitation wavelengths)) that is about an order-of-magnitude lower than resins that include a combination of a free radical photoinitiator and a cationic photoinitiator.

The resin composition disclosed herein may also be more readily photobleached, which would render the cured resin composition permanently unable to autofluoresce (i.e., any autofluorescence that does occur is below a threshold limit of detection or does not interfere with sequencing detection processes).

As mentioned herein, the examples of the cured resin composition disclosed herein have minimal blue and green emissions, and also exhibit very low or no autofluorescence when exposed to blue and green excitation wavelengths. As used herein, blue emission wavelengths include from about 463 nm to about 514, and green emission wavelengths include from about 583 nm to about 660 nm. Also as used herein, blue excitation wavelengths include from about 380 nm to about 480 nm, and green excitation wavelengths include from about 510 nm to about 560 nm. In another example, the blue excitation wavelengths range from about 440 nm to about 457 nm or the green excitation wavelengths range from about 519 nm to about 535 nm. In still another example, the blue excitation wavelengths range from about 400 nm to about 480 nm.

In some instances, the cured resin composition is described as having no fluorescence (emission of light) when exposed to blue excitation wavelengths and/or green excitation wavelengths. No fluorescence or no autofluorescence means that the level of fluorescence is below a threshold limit of detection. No fluorescence or no autofluorescence, as the terms are defined herein, may occur when the cured resin composition has been photobleached. In other instances, the cured resin composition fluoresces (emits light) when exposed to blue excitation wavelengths and/or green excitation wavelengths. In these instances, the term "low autofluorescence" may mean that the emission level (of the cured resin when exposed to blue excitation wavelengths and/or green excitation wavelengths) is above the threshold limit of detection, but is low enough to be considered noise, and the noise does not interfere with the identification of cluster signals during sequencing (e.g., the levels of autofluorescence enable signal to noise ratios (SNRs) that are high enough so that signals from individual clusters can be resolved during sequencing).

It is to be understood that the definition of "low" or "low level", in terms of quantifying the autofluorescence, may vary depending upon the tool used to measure the autofluorescence and/or lamps used to provide the excitation radiation. For example, when an Amersham TYPHOON™ (formerly TYPHOON™ FLA 7000) (available from GE Healthcare Life Sciences) is used to measure the autofluorescence of the cured resin composition upon exposure to blue excitation wavelengths, the low autofluorescence corresponds with a grey value of less than 25,000. For another example, when the Amersham TYPHOON™ is used to measure the autofluorescence of the cured resin composition upon exposure to blue excitation wavelengths, the low autofluorescence corresponds with a grey value of less than 5,000. For still another example, when Amersham TYPHOON™ is used to measure the autofluorescence of the cured resin composition upon exposure to green excitation wavelengths, the low autofluorescence corresponds with a grey value of less than 10,000. For yet a further example, when Amersham TYPHOON™ is used to measure the autofluorescence of the cured resin composition upon exposure to green excitation wavelengths, the low autofluorescence corresponds with a grey value of less than 2,500.

Autofluorescence may also be measured using a spectrometer based tool. Discussion of an example of a spectrometer based tool is found in Example 2 below. In an example, when a spectrometer based tool is used to measure the autofluorescence of the cured resin composition upon exposure to blue excitation wavelengths, the low autofluorescence corresponds with a fluorescence intensity (in arbitrary units (AU)) of less than about 400 AU. In another example, when a spectrometer based tool is used to measure the autofluorescence of the cured resin composition upon exposure to green excitation wavelengths, the low autofluorescence corresponds with a fluorescence intensity (in arbitrary units (AU)) of less than about 500 AU.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

An "acrylamide" is a functional group with the structure

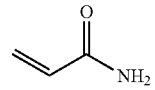

or a monomer including an acrylamide group with that structure. An acrylamide may be the chemical compound acylamide with a substituent in place of one or more hydrogen atoms (e.g., methacrylamide). Examples of the monomer including an acrylamide group include azido acetamido pentyl acrylamide:

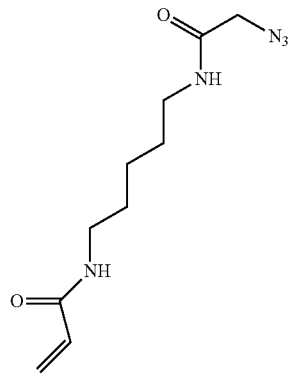 [SMILES: C=CC(=O)NCCCCCNC(=O)CN=[N+]=[N-]]

and N-isopropylacrylamide:

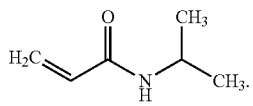

Other acrylamide monomers may be used.

An "aldehyde," as used herein, is an organic compound containing a functional group with the structure —CHO, which includes a carbonyl center (i.e., a carbon double-bonded to oxygen) with the carbon atom also bonded to hydrogen and an R group, such as an alkyl or other side chain. The general structure of an aldehyde is:

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

An "amino" functional group refers to an —NR$_a$R$_b$ group, where R$_a$ and R$_b$ are each independently selected from hydrogen (e.g., $\sim\!\!\diagdown\!\!\diagup$NH$_2$), C1-C6 alkyl, C2-C6 alkenyl, C2-C6 alkynyl, C3-C7 carbocyclyl, C6-C10 aryl, 5-10 membered heteroaryl, and 5-10 membered heterocyclyl, as defined herein.

As used herein, the term "attached" refers to the state of two things being joined, fastened, adhered, connected or bound to each other, either directly or indirectly. For example, a nucleic acid can be attached to a polymer coating by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to —N$_3$.

As used herein, a "bonding region" refers to an area on a substrate that is to be bonded to another material, which may be, as examples, a spacer layer, a lid, another substrate, etc., or combinations thereof (e.g., a spacer layer and a lid). The bond that is formed at the bonding region may be a chemical bond (as described above), or a mechanical bond (e.g., using a fastener, etc.).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms. Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, "cycloalkenyl" or "cycloalkene" means a carbocyclyl ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkyl" means any univalent groups derived from cycloalkanes by removal of a hydrogen atom from a ring carbon atom (e.g., from a cycloalkane). An example includes 2-methylcyclopropyl.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

As used herein, the term "depression" refers to a discrete concave feature in a patterned resin having a surface opening that is at least partially surrounded by interstitial region(s) of the patterned resin. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or a trench/line/trough. The depression may also have more complex architectures, such as ridges, step features, etc.

As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber/flow channel can include one or more transparent surfaces allowing for the optical detection of arrays, optically labeled molecules, or the like, at the depression.

As used herein, a "flow channel" may be an area defined between two bonded components, which can selectively receive a liquid sample. In some examples, the flow channel may be defined between a patterned resin and a lid, and thus may be in fluid communication with one or more depressions defined in the patterned resin.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a

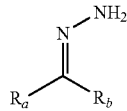

group in which $R_a$ and $R_b$ are each independently selected from hydrogen

C1-C6 alkyl, C2-C6 alkenyl, C2-C6 alkynyl, C3-C7 carbocyclyl, C6-C10 aryl, 5-10 membered heteroaryl, and 5-10 membered heterocyclyl, as defined herein.

As used herein, "hydroxy" or "hydroxyl" refers to an —OH group.

As used herein, the term "interstitial region" refers to an area on a surface (e.g., of a patterned resin) that separates depressions. For example, an interstitial region can separate one feature of an array from another feature of the array. The two features that are separated from each other can be discrete, i.e., lacking physical contact with each other. In another example, an interstitial region can separate a first portion of a feature from a second portion of a feature. In many examples, the interstitial region is continuous whereas the features are discrete, for example, as is the case for a plurality of wells defined in an otherwise continuous surface. In other examples, the interstitial regions and the features are discrete, for example, as is the case for a plurality of trenches separated by respective interstitial regions. The separation provided by an interstitial region can be partial or full separation. Interstitial regions may have a surface material that differs from the surface material of the features defined in the surface. For example, features of an array can have an amount or concentration of a polymer coating and primer(s) that exceeds the amount or concentration present at the interstitial regions. In some examples, the polymer coating and primer(s) may not be present at the interstitial regions.

"Nitrile oxide," as used herein, means a "$R_aC{\equiv}N^+O^-$" group in which $R_a$ is defined herein. Examples of preparing nitrile oxide include in situ generation from aldoximes by treatment with chloramide-T or through action of base on imidoyl chlorides [RC(Cl)=NOH] or from the reaction between hydroxylamine and an aldehyde.

"Nitrone," as used herein, means a

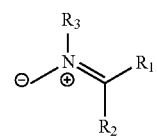

group in which $R_1$, $R_2$, and $R_3$ may be any of the $R_a$ and $R_b$ groups defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

As used herein, a "photoacid generator" (PAG) is a molecule that releases protons upon exposure to radiation. PAGs generally undergo proton photodissociation irreversibly.

As used herein, a "photoinitiator" (PI) is a molecule that undergoes a photoreaction upon absorption of radiation, thereby producing reactive species. Photoinitiators are capable of initiating or catalyzing chemical reactions that result in changes in the solubility and/or physical properties of formulations.

As used herein, the "primer" is defined as a single stranded nucleic acid sequence (e.g., single strand DNA or single strand RNA). Some primers, which may be referred to as amplification primers, serve as a starting point for template amplification and cluster generation. Other primers, which may be referred to as sequencing primers, serve as a starting point for DNA or RNA synthesis. The 5' terminus of the primer may be modified to allow a coupling reaction with a functional group of a polymer coating. The primer length can be any number of bases long and can include a variety of non-natural nucleotides. In an example, the sequencing primer is a short strand, ranging from 10 to 60 bases, or from 20 to 40 bases.

A "spacer layer," as used herein refers to a material that bonds two components together. In some examples, the spacer layer can be a radiation-absorbing material that aids in bonding, or can be put into contact with a radiation-absorbing material that aids in bonding.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

In the examples disclosed herein, the resin complex includes a free radical curable resin matrix including an acrylate and a siloxane, and a free radical photoinitiator wherein, when cured, the resin composition has no or low autofluorescence when exposed to blue excitation wavelengths ranging from about 380 nm to about 480 nm or green excitation wavelengths ranging from about 510 nm to about 560 nm.

The free radical curable resin matrix includes an acrylate group and a siloxane group. As used herein the term "acrylate" refers to a "CH$_2$=CHCOO—" functional group (i.e., 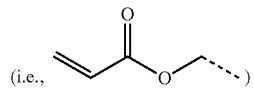 )

or a "CH$_2$=C(CH$_3$)COO—" functional group (i.e., methacrylate). Acrylates include substituted variations thereof (e.g., methacrylate is an example of an acrylate). A siloxane group is a functional group that includes an Si—O—Si linkage. The molecular weight and the cross linking density of the monomer(s) of the free radical curable resin matrix may vary, as long as the resin composition is imprintable via the methods disclosed herein. In an example, the molecular weight of the monomer(s) of the free radical curable resin matrix may range from about 0.5 kDa to about 5 kDa, or from about 1 kDa to about 4.5 kDa. The cross linking functionality, and in turn, the cross linking density, depends on the number of arms (e.g., di, tri, tetra) of the monomer.

Examples of the free radical curable resin matrix are matrices comprising an acrylate selected from the group consisting of:

i) 1,3-bis(3-methacryloxypropyl) tetramethyldisiloxane:

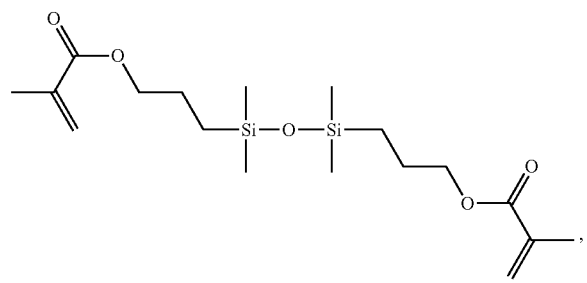 [SMILES: C=C(C)C(=O)OCCC[Si](C)(C)O[Si](C)(C)CCCOC(=O)C(=C)C]

ii) methacryloxypropyl-terminated polydimethylsiloxane:

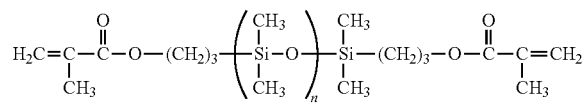

(wherein n ranges from 1 to 1000, or any range in between, for example, from 1 to 500, or 1 to 100, or 2 to 50, 1 to 10, 1 to 2, etc.), iii) tetramethyl tetrakis[3-acryloxypropyl]cyclotetrasiloxane:

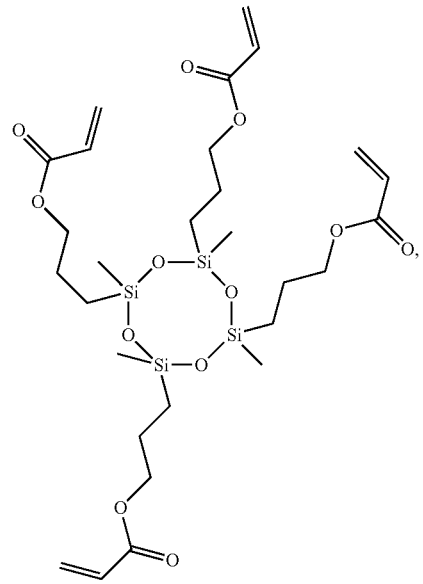 [SMILES: C=CC(=O)OCCC[Si]1(C)O[Si](C)(CCCOC(=O)C=C)O[Si](C)(CCCOC(=O)C=C)O[Si](C)(CCCOC(=O)C=C)O1]

iv) methacryl polyhedral oligomeric silsesquioxane (POSS):

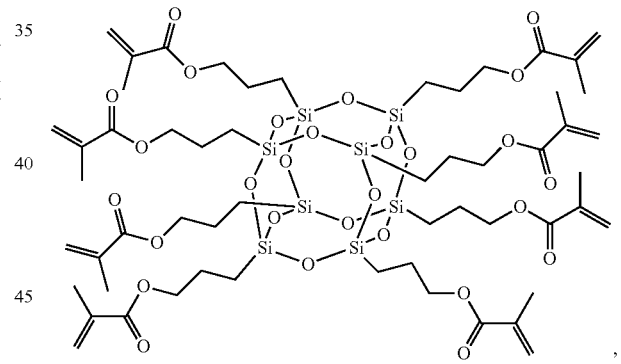

v) acryl polyhedral oligomeric silsesquioxane:

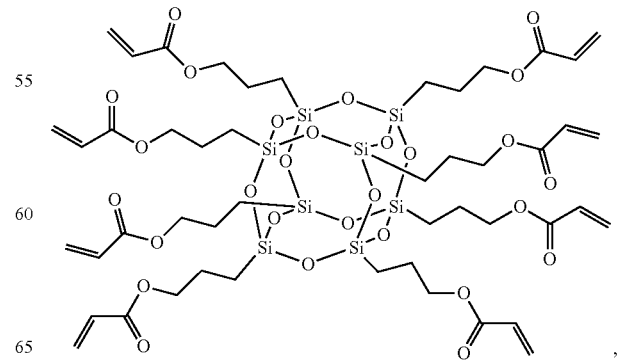

vi) acryloxypropyl methylsiloxane homopolymer:

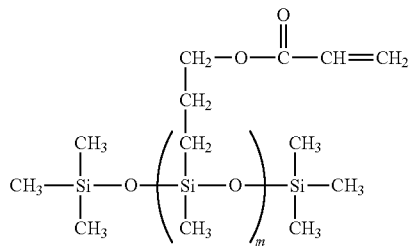

(wherein m ranges from 1 to 1000 or any range in between, for example, 1 to 500, 30 to 200, 30 to 100, etc.), and vii) combinations thereof. When combinations are used, it is to be understood that any two or more of the listed free radical curable resin matrices may be used together in the resin composition as long they both are soluble in the solvent used in the composition.

The photoinitiator in the example resin compositions disclosed herein may be any free radical generating photoinitiator that exhibits low autofluorescence in the cured resin.

In some examples, the free radical photoinitiator is 2-ethyl-9,10-dimethoxyanthracene:

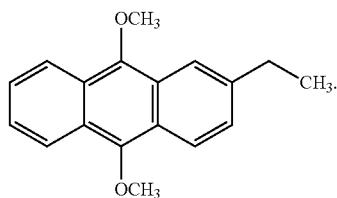 [SMILES: CCc1ccc2c(OC)c3ccccc3c(OC)c2c1]

In other examples, the free radical photoinitiator is 2,2-dimethoxy-2-phenylacetophenone:

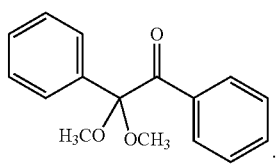 [SMILES: COC(OC)(C(=O)c1ccccc1)c1ccccc1]

In yet other examples, the free radical photoinitiator is 2-ethoxy-2-phenylacetophenone (a.k.a., benzoin ethyl ether):

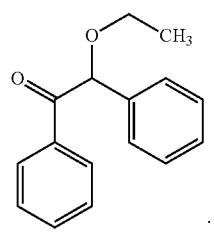 [SMILES: CCOC(C(=O)c1ccccc1)c1ccccc1]

In still other examples, the free radical photoinitiator is a phosphine oxide. When the phosphine oxide is used, it may be selected from the group consisting of:

i) diphenyl(2,4,6-trimethylbenzoyl)phosphine oxide:

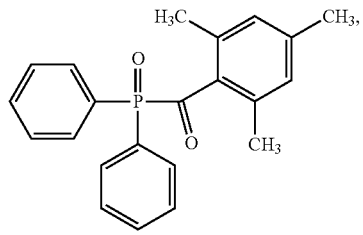 [SMILES: Cc1cc(C)c(C(=O)P(=O)(c2ccccc2)c2ccccc2)c(C)c1]

ii) a blend of diphenyl(2,4,6-trimethylbenzoyl)phosphine oxide and 2-hydroxy-2-methylpropiophenone:

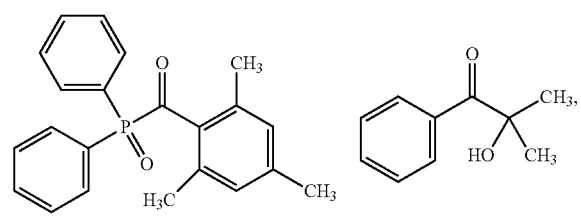

iii) phenylbis(2,4,6-,trimethylbenzoyl)phosphine oxide:

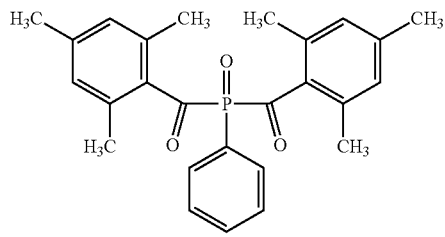

iv) ethyl(2,4,6-trimethylbenzoyl)phenylphosphinate:

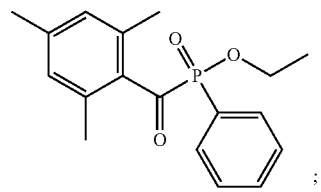 [SMILES: CCOP(=O)(C(=O)c1c(C)cc(C)cc1C)c1ccccc1]

and v) combinations thereof. When combinations are used, it is to be understood that any two or more of the listed free radical photoinitiators may be used together in the resin composition as long they both are soluble in the solvent used in the composition.

The resin composition may be made by mixing the free radical curable resin matrix with the photoinitiator. In an example, a weight % ratio of the free radical curable resin matrix to the photoinitiator ranges from about 99.8:0.2 to 90:10. In another example, a weight % ratio of the free radical curable resin matrix to the photoinitiator ranges from about 98:2 to 95:5. In still another example, a weight % ratio of the free radical curable resin matrix to the photoinitiator ranges from about 96:4 to 99:1. When lower amounts of the photoinitiator are included, the UV cure time may be increased to allow for complete reaction.

It is to be understood that the weight % ratio of the free radical curable resin matrix to the photoinitiator may be higher or lower depending, at least in part, upon the free radical curable resin matrix component(s) that are used.

In order to deposit the resin composition, these components (the free radical curable resin matrix and the photoinitiator) may be diluted in a suitable solvent (to achieve a desired viscosity for the deposition technique used), such as propylene glycol monomethyl ether acetate (PGMEA), toluene, dimethyl sulfoxide (DMSO), tetrahydrofuran (THF), etc. In an example, the concentration of the free radical curable resin matrix in the solvent ranges from about 15 weight % (wt %) to about 56 wt %, and the concentration of the photoinitiator in the solvent ranges from about 1 wt % to about 10 wt %, although it is believed that the upper limits may be higher depending upon the respective solubility of the free radical curable resin matrix and photoinitiator in the solvent that is selected. In an example, the solvent is PGMEA. The total concentration (including the free radical curable resin matrix and the photoinitiator (and a polyacrylate or surfactant, if used)) of the final resin composition may range from about 16 wt % to about 66 wt %. The amount of solvent may range from about 34 wt % to about 84 wt %.

In some examples, the resin composition may further include a dark quencher or an electron acceptor. A dark quencher is a substance that absorbs light energy from a fluorophore and dissipates the energy as heat. This provides a non-radiative route for relaxation of excited state species. In the examples disclosed herein, the dark quencher selected should be capable absorbing blue and/or green autofluorescence from the cured resin composition. An electron acceptor can also induce fluorescence quenching.

In an example, the dark quencher may comprise azo-dyes. In a further example, the dark quencher comprises a substituted azobenzene derivative selected from the group consisting of: 4-dimethylaminoazobenzene-4'-carboxylic acid:

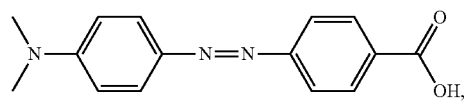 [SMILES: CN(C)c1ccc(N=Nc2ccc(C(=O)O)cc2)cc1]

dabcyl azide:

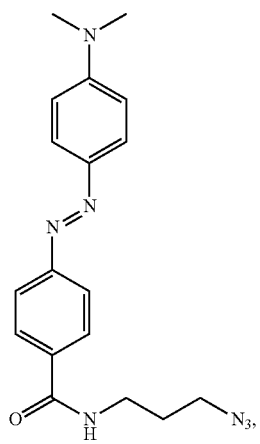 [SMILES: CN(C)c1ccc(/N=N/c2ccc(C(=O)NCCCN=[N+]=[N-])cc2)cc1]

dabsyl-azide:

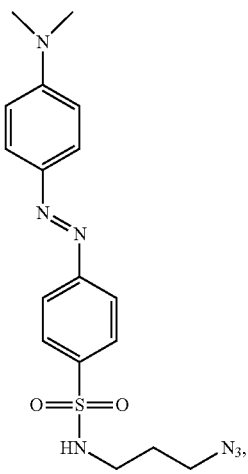 [SMILES: CN(C)c1ccc(/N=N/c2ccc(S(=O)(=O)NCCCN=[N+]=[N-])cc2)cc1]

disperse red 19:

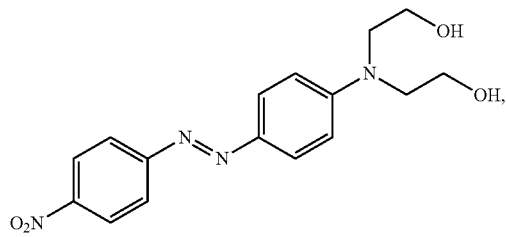 [SMILES: O=[N+]([O-])c1ccc(/N=N/c2ccc(N(CCO)CCO)cc2)cc1]

carbon black pigment (CBP) additives, a black dye-based quencher (such as, e.g., TRUEBLACK® lipofuscin autofluorescence quencher, 20X in DMF), and combinations thereof. Examples of suitable electron acceptors may include [5,6]-fullerene-C70:

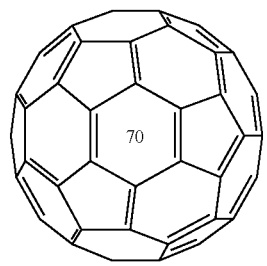 [SMILES: c1c2c3c4c(cc5c6c4c4c7c3c3c1Cc1cc8cc9cc%10cc(c%11c%10c%10c9c9c8c1c3c7c9c%10c4c%116)C5)C2]

or fullerene-C60:

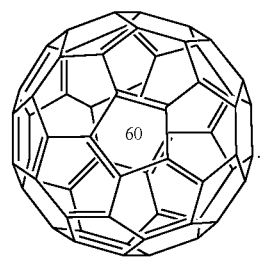

In an example, the dark quencher or electron acceptor may be present in an amount ranging from about 0.1 wt % to about 10 wt %, based on a total weight of the resin composition.

Some other examples of the resin composition may further include a polyacrylate or a surfactant. An example of a commercially available polyacrylate is BYK®-350 (available from BYK Additives & Instruments). Any biocompatible surfactant may be used, such as TWEEN® surfactants (e.g., polyethylene sorbitol esters (TWEEN® 80) and polyoxyethylene sorbitol esteris (TWEEN® 20) from Uniqema Americas LLC); TRITON™ X-100 (Octylphenol Ethoxylate from The Dow Chemical Co.), and polymeric surfactants available from BYK Additives and Instruments. In an example, the polyacrylate or surfactant may be present in the resin composition in an amount ranging from about 0.4 wt % total solids to about 1.6 wt % total solids.

In some examples, the resin composition may further include an epoxy resin matrix in combination with the free radical curable resin matrix. Unlike the free radical curable resin matrix disclosed herein, epoxy resin matrices involve a two-part curing system, where the free radicals generated by the photoinitiator disclosed herein react with a photoacid generator, which decomposes to generate a superacid, which, in turn, initiates the polymerization and/or crosslinking of the epoxy resin matrix component(s). As such, in examples that include an epoxy in addition to the free radical curable resin matrix, it is to be understood that the resin composition also includes a photoacid generator. In these examples, it is believed that the Norrish Type II anthracene derivative photoinitiator and the Norrish Type I acetophenone or phosphine oxide photoinitiators disclosed herein can generate radicals with UVA exposure, which can contribute to the two-part curing system with the photoacid generator, without undergoing intramolecular interactions that lead to undesirable autofluorescence in blue and/or green excitation wavelengths of interest. Examples of suitable epoxy resin matrices and photoacid generators that may be added to the resin composition disclosed herein will now be described.

Any epoxy monomer that can crosslink with the free radical curable resin disclosed herein may be used. Examples of suitable epoxy resin matrices include:
i) an epoxy functionalized polyhedral oligomeric silsesquioxane (POSS) (described further hereinbelow);
ii) trimethylolpropane triglycidyl ether:

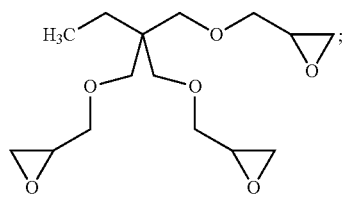 [SMILES: CCC(COCC1CO1)(COCC1CO1)COCC1CO1]

iii) tetrakis(epoxycyclohexyl ethyl)tetramethyl cyclotetrasiloxane:

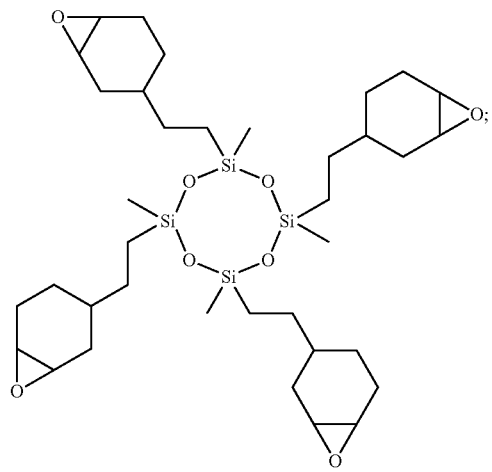 [SMILES: C[Si]1(CCC2CCC3OC3C2)O[Si](C)(CCC2CCC3OC3C2)O[Si](C)(CCC2CCC3OC3C2)O[Si](C)(CCC2CCC3OC3C2)O1]

iv) a copolymer of (epoxycyclohexylethyl)methylsiloxane and dimethylsiloxane:

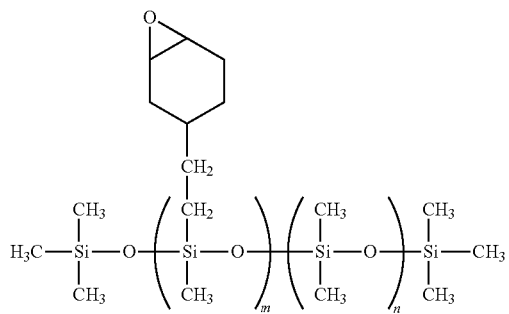

(wherein a ratio of m:n ranges from 8:92 to 10:90);
v) 1,3-bis[2-(3,4-epoxycyclohexyl) ethyl] tetramethyl disiloxane:

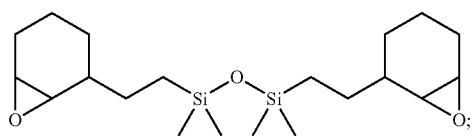 [SMILES: C[Si](C)(CCC1CCCC2OC12)O[Si](C)(C)CCC1CCCC2OC12]

vi) 1,3-bis(glycidoxypropyl)tetramethyl disiloxane:

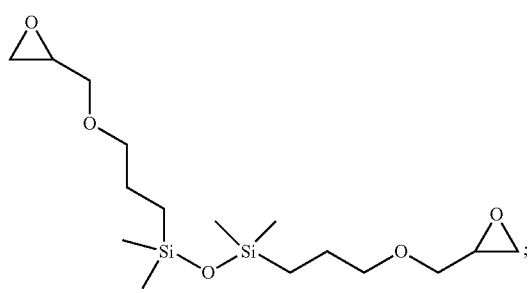 [SMILES: C[Si](C)(CCCOCC1CO1)O[Si](C)(C)CCCOCC1CO1]

and vii) combinations thereof. When combinations are used, it is to be understood that any two or more of the listed epoxy resin matrices may be used together in the resin composition disclosed herein.

The epoxy functionalized polyhedral oligomeric silsesquioxane includes a polyhedral oligomeric silsesquioxane (POSS) core that is functionalized with epoxy groups. As used herein, the term "polyhedral oligomeric silsesquioxane" (POSS) refers to a chemical composition that is a hybrid intermediate ($RSiO_{1.5}$) between that of silica ($SiO_2$) and silicone ($R_2SiO$). An example of POSS can be that described in Kehagias et al., Microelectronic Engineering 86 (2009), pp. 776-778, which is incorporated by reference in its entirety. The composition is an organosilicon compound with the chemical formula $[RSiO_{3/2}]_n$, where the R groups can be the same or different. The resin composition disclosed herein may comprise one or more different cage or core structures as monomeric units. In some instances, the structure includes a polyoctahedral cage or core structure. For example, the polyhedral structure may be a $T_8$ structure, such as:

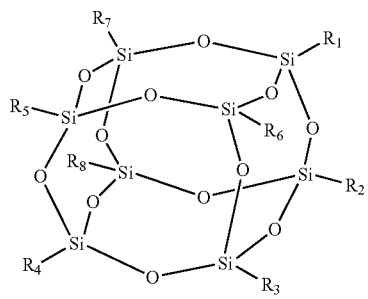

and represented by:

    $T_8$

This monomeric unit typically has eight arms of functional groups $R_1$ through $R_8$.

The monomeric unit may have a cage structure with 10 silicon atoms and 10 R groups, referred to as $T_{10}$, such as:

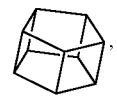    $T_{10}$ or may have a cage structure with 12 silicon atoms and 12 R groups, referred to as $T_{12}$, such as:

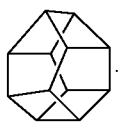    $T_{12}$

The POSS-based material may alternatively include $T_6$, $T_{14}$, or $T_{16}$ cage structures. The average cage content can be adjusted during the synthesis, and/or controlled by purification methods, and a distribution of cage sizes of the monomeric unit(s) may be used in the examples disclosed herein. As examples, any of the cage structures may be present in an amount ranging from about 30% to about 100% of the total POSS monomeric units used. The POSS-based material may be a mixture of cage structures along with open and partially open cage structures. Thus, a POSS-based resin precursor or resin may include epoxy POSS materials, which may be a mixture of silsesquioxane configurations. For example, any POSS material described herein may be a mixture of discrete POSS cages and non-discrete silsesquioxane structures and/or incompletely condensed, discrete structures, such as polymers, ladders, and the like. The partially condensed materials would therefore include epoxy R groups as described herein at some silicon vertices, but some silicon atoms would not be substituted with the R groups and could be substituted instead with OH groups. In some examples, the POSS materials comprise a mixture of various forms, such as:

(a)

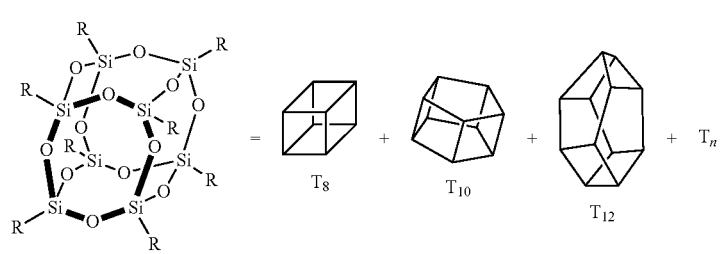

Condensed cages (b)

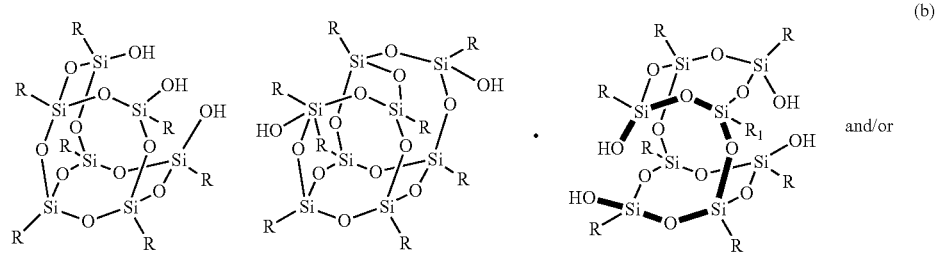    and/or

Incompletely Condensed cages

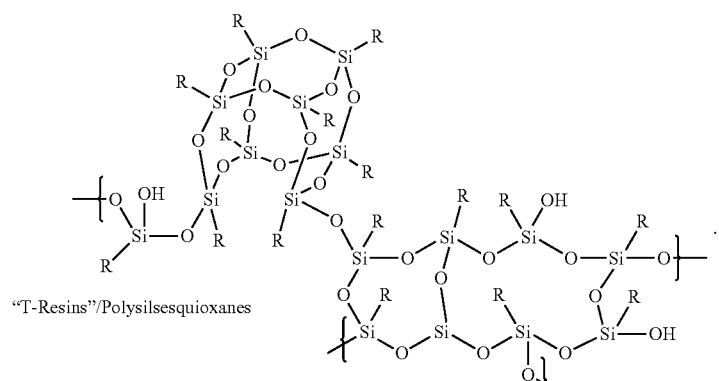

"T-Resins"/Polysilsesquioxanes

Non-cage content Large & ill-defined structure

In the examples disclosed herein, at least one of $R_1$ through $R_8$ or $R_{10}$ or $R_{12}$ comprises an epoxy, and thus the POSS is referred to as an epoxy POSS. In some examples, a majority of the arms, such as the eight, ten, or twelve arms, or R groups, comprise epoxy groups. In other examples, $R_1$ through $R_8$ or $R_{10}$ or $R_{12}$ are the same, and thus each of $R_1$ through $R_8$ or $R_{10}$ or $R_{12}$ comprises an epoxy group. In still other examples, $R_1$ through $R_8$ or $R_{10}$ or $R_{12}$ are not the same, and thus at least one of $R_1$ through $R_8$ or $R_{10}$ or $R_{12}$ comprises epoxy and at least one other of $R_1$ through $R_8$ or $R_{10}$ or $R_{12}$ is a non-epoxy functional group, which in some cases is selected from the group consisting of an azide/azido, a thiol, a poly(ethylene glycol), a norbornene, a tetrazine, acrylates, and methacrylates, or further, for example, alkyl, aryl, alkoxy, and haloalkyl groups. In some aspects, the non-epoxy functional group is selected to increase the surface energy of the resin. In these other examples, the ratio of epoxy groups to non-epoxy groups ranges from 7:1 to 1:7, or 9:1 to 1:9, or 11:1 to 1:11. In any of the examples, disubstituted or monosubstituted (terminal) epoxy group(s) allow the monomeric unit to polymerize into a cross-linked matrix upon initiation using ultraviolet (UV) light and an acid. In some aspects, the epoxy POSS comprises terminal epoxy groups. An example of this type of POSS is glycidyl POSS having the structure:

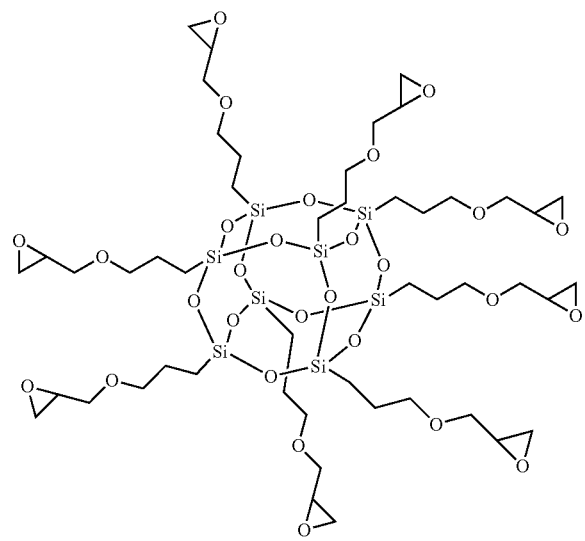 [SMILES: C(COCC1CO1)C[Si]12O[Si]3(CCCOCC4CO4)O[Si]4(CCCOCC5CO5)O[Si](CCCOCC5CO5)(O1)O[Si]1(CCCOCC5CO5)O[Si](CCCOCC5CO5)(O2)O[Si](CCCOCC2CO2)(O3)O[Si](CCCOCC2CO2)(O4)O1]

Another example of this type of POSS is epoxycyclohexyl ethyl functionalized POSS having the structure:

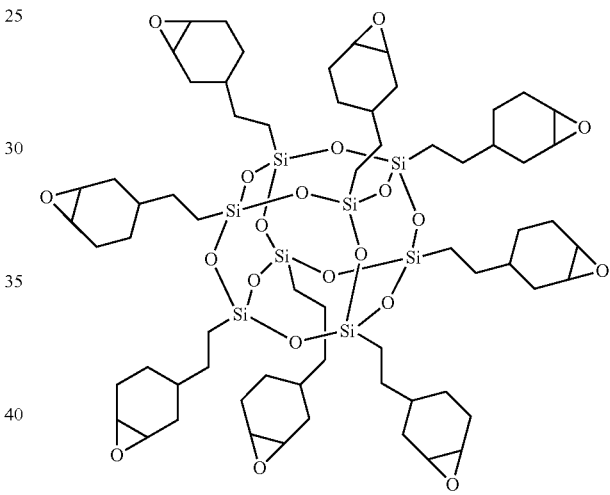

One example of the epoxy resin matrix disclosed herein includes a combination of two epoxy POSS compounds, where the combination includes glycidyl POSS and epoxycyclohexyl ethyl functionalized POSS.

In the examples disclosed herein, the epoxy POSS may also be a modified epoxy POSS, that includes a controlled radical polymerization (CRP) agent and/or another functional group of interest incorporated into the resin or core or cage structure as one or more of the functional group $R_1$ through $R_8$ or $R_{10}$ or $R_{12}$.

As mentioned above, when an epoxy resin matrix is used in combination with the free radical curable resin matrix, the resin composition also includes a photoacid generator. It is believed that any suitable photoacid generator that will not undergo undesirable intramolecular interactions with the free radical photoinitiator disclosed herein may be used. Examples of suitable photoacid generators may include benzyl, imino ester, conjugated imino ester, spiropyran, teraylene-based, two-photon, and organometallic PAG systems. Some specific examples of suitable photoacid generators are selected from the group consisting of:

i) N-hydroxynaphthalimide triflate:

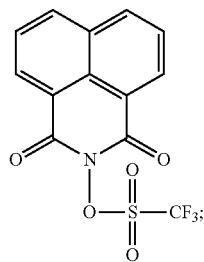 [SMILES: O=C1c2cccc3cccc(c23)C(=O)N1OS(=O)(=O)C(F)(F)F]

ii) triarylsulfonium hexafluorophosphate salts, mixed:

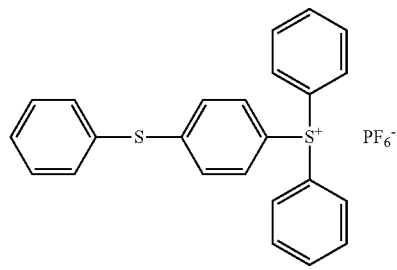

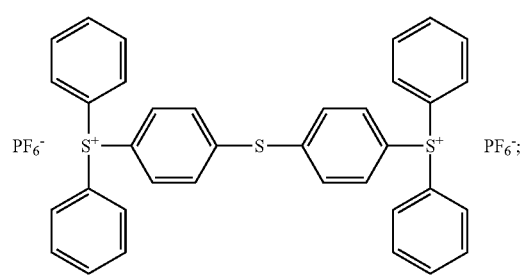

iii) triarylsulfonium hexafluoroantimonate salts, mixed:

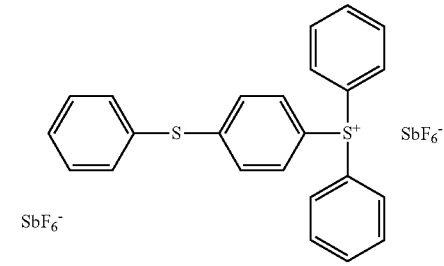

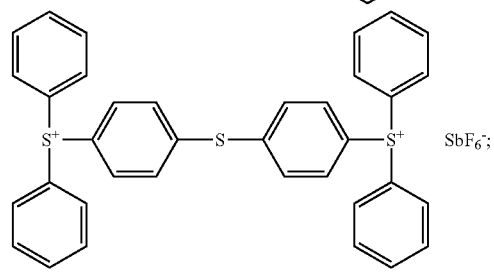

iv) 1-naphthyl diphenylsulfonium triflate (NDS-TF):

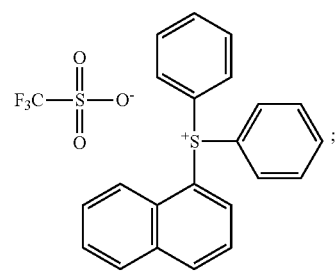 [SMILES: O=S(=O)([O-])C(F)(F)F ; c1ccc([S+](c2ccccc2)c2cccc3ccccc23)cc1]

v) (4-phenylthiophenyl)diphenylsulfonium triflate:

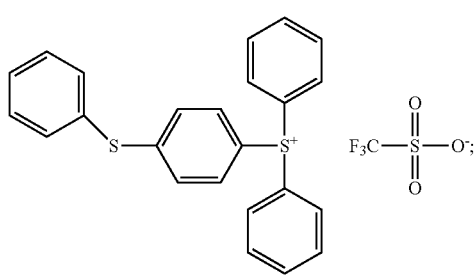

vi) bis-(4-methylphenyl)iodonium hexafluorophosphate:

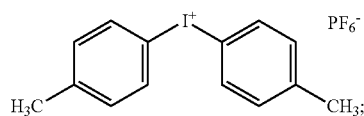

vii) bis(4-tert-butylphenyl)iodonium hexafluorophosphate:

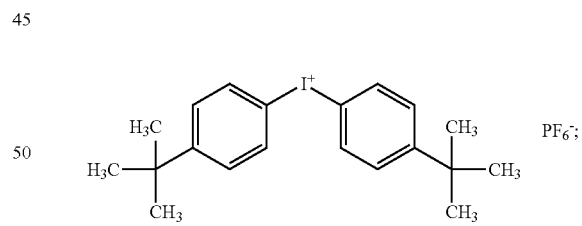

viii) (2-methylphenyl)(2,4,6-trimethylphenyl)iodonium triflate:

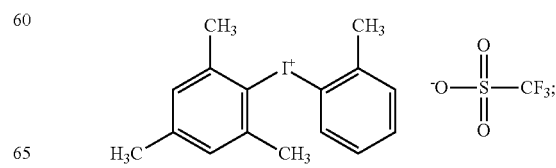

xi) bis(2,4,6-trimethylphenyl)iodonium triflate:

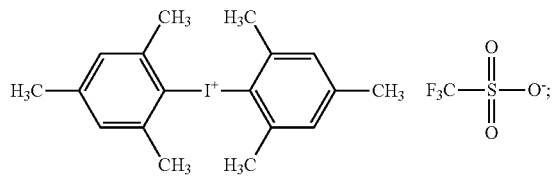

x) bis-(4-dedecylphenyl)iodonium hexafluoroantimonate salt:

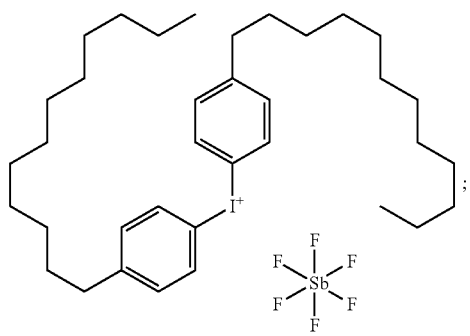

and xi) combinations thereof. Combinations of the photoacid generators may be used as long as they are soluble in the selected solvent.

In an example of the resin composition including the epoxy resin matrix and the photoacid generator, a weight % ratio of the epoxy resin matrix to the photoacid generator ranges from about 99.8:0.2 to 90:10. In another example, a weight % ratio of the epoxy resin matrix to the photoacid generator ranges from about 98:2 to 95:5. In still another example, a weight % ratio of the epoxy resin matrix to the photoacid generator ranges from about 96:4 to 99:1. When lower amounts of the photoacid generator are included, the UV cure time may be increased to allow for complete reaction.

It is to be understood that the weight % ratio of the epoxy resin matrix to the photoacid generator may be higher or lower depending, at least in part, upon the epoxy resin matrix component(s) that are used.

Any example of the resin composition disclosed herein may be used in the formation of the flow cell. An example of a method 100 for making an example of a flow cell is shown in FIG. 1. As shown in FIG. 1, the method 100 includes depositing a resin composition on a substrate, the resin composition including a free radical curable resin matrix including an acrylate and a siloxane and a free radical photoinitiator (reference numeral 102); nanoimprinting the deposited resin composition using a working stamp (reference numeral 104); and curing the deposited resin composition to form a cured, patterned resin, wherein the cured, patterned resin has low or no autofluorescence when exposed to blue excitation wavelengths ranging from about 380 nm to about 480 nm or green excitation wavelengths ranging from about 510 nm to about 560 nm (reference numeral 106). The resulting flow cell includes a substrate and a cured, patterned resin on the substrate, the cured, patterned resin including depressions separated by interstitial regions, and the cured, patterned resin having been formed from an example of the resin composition disclosed herein.

While not shown in FIG. 1, examples of the method 100 may further include applying a polymer coating in the depressions, and grafting a primer to the polymer coating. The method 100, including these additional processes, will now be described further in reference to FIGS. 2A through 2E.

FIG. 2A depicts a substrate 12, and FIG. 2B depicts a resin composition 14 deposited on the substrate 12.

Examples of suitable substrate 12 include epoxy siloxane, glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like. The substrate 12 may also be glass or silicon, with a coating layer of tantalum oxide or another ceramic oxide at the surface.

In an example, the substrate 12 may have a diameter ranging from about 2 mm to about 300 mm, or a rectangular sheet or panel having its largest dimension up to about 10 feet (~3 meters). In an example, the substrate 12 is a wafer having a diameter ranging from about 200 mm to about 300 mm. In another example, the substrate 12 is a die having a width ranging from about 0.1 mm to about 10 mm. While example dimensions have been provided, it is to be understood that a substrate 12 with any suitable dimensions may be used. For another example, a panel may be used that is a rectangular substrate 12, which has a greater surface area than a 300 mm round wafer.

The resin composition 14 may be any examples of the resin composition described herein, which includes the free radical curable resin matrix including an acrylate and a siloxane and the free radical initiator (or an epoxy resin matrix in combination with the free radical curable resin matrix). The resin composition 14 may be deposited on the substrate 12 using any suitable application technique, which may be manual or automated. As examples, the deposition of the resin composition 14 may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, aerosol printing, screen printing, microcontact printing, inkjet printing, or the like. In one example, spin coating is used to deposit the resin composition 14.

After the resin composition 14 is deposited, it may be softbaked to remove excess solvent. The deposited resin composition 14 is then patterned, using any of the patterning techniques mentioned herein. In the example shown in FIG. 2B, nanoimprint lithography is used to pattern the resin composition 14. A nanoimprint lithography mold or working stamp 20 is pressed against the layer of the resin composition 14 to create an imprint on the resin composition 14. In other words, the resin composition 14 is indented or perforated by the protrusions of the working stamp 20. In an example, the resin composition 14 may be cured with the working stamp 20 in place.

For the resin compositions 14 disclosed herein, curing may be accomplished by exposure to actinic radiation, such as ultraviolet (UV) radiation (e.g., metal halide light sources, mercury vapor light sources, UV emitting LED light sources, etc.). Curing promotes radical formation due to the presence of the photoinitiator, and these radicals are used to cure the acrylate portion of the resin composition. As such, curing promotes polymerization and/or cross-linking of the resin composition 14. As an example, curing may include a single UV exposure stage, or may include multiple stages, including a softbake (e.g., to drive off solvent(s)) and then UV exposure. When included, the softbake may take place at a lower temperature, ranging from about 50° C. to about 150° C. for greater than 0 seconds to about 3 minutes, and may take place before the working stamp 20 is placed in the resin composition 14. In an example, the softbake time ranges from about 30 seconds to about 2.5 minutes. During the softbake, one or more chemical processes may be taking place that further contribute to a reduction in the autofluorescence. Example chemical processes may include evaporation of some of resin composition material(s), sublimation of some of resin composition material(s), polymerization of some of the resin composition material(s), and/or combinations thereof. Some examples may also include a hardbake. However, the curing mechanism of the resin composition 14 disclosed herein is so fast, that the resin composition 14 may be fully cured without a hardbake. If performed, the working stamp 20 is released/detached before the hardbake, e.g., so that the working stamp 20 does not bond to the cured resin composition 14. If performed, the duration of the hardbake may last from about 5 seconds to about 10 minutes at a temperature ranging from about 100° C. to about 300° C. Hardbaking may be performed, for example, to remove residual solvent(s) from the resin composition 14, to further polymerization of some of the resin composition material(s) (and thus enhance the extent of curing), and/or to further reduce the autofluorescence. Examples of devices that can be used for softbaking and/or hardbaking include a hot plate, oven, etc.

After the release of the working stamp 20, topographic features, e.g., the depressions 16, are in the resin composition 14. As shown in FIG. 2C, the resin composition 14 having the depressions 16 defined therein is referred to as the cured, patterned resin 14'. In some examples, the cured, patterned resin 14' may be subject to further hard baking, e.g., to aid in locking in the imprinted topography, and/or to further reduce fluorescence. In some examples, the additional hard baking may be performed at a temperature ranging from about 60° C. to about 300° C.

The chemical make-up of the cured, patterned resin 14' depends upon the free radical curable resin matrix or matrices and the free radical photoinitiator(s) used in the resin composition 14.

As shown in FIG. 2C, the cured, patterned resin 14' includes the depressions 16 defined therein, and interstitial regions 22 separating adjacent depressions 16. In the examples disclosed herein, the depressions 16 become functionalized with a polymer coating 18 (FIGS. 2C-2D) and primers 24 (FIGS. 2E-2F), while portions of the interstitial regions 22 may be used for bonding but will not have the polymer coating 18 or the primer(s) 24 thereon.

Many different layouts of the depressions 16 may be envisaged, including regular, repeating, and non-regular patterns. In an example, the depressions 16 are disposed in a hexagonal grid for close packing and improved density. Other layouts may include, for example, rectilinear (i.e., rectangular) layouts (e.g., lines or trenches), triangular layouts, and so forth. In some examples, the layout or pattern can be an x-y format of depressions 16 that are in rows and columns. In some other examples, the layout or pattern can be a repeating arrangement of depressions 16 and/or interstitial regions 22. In still other examples, the layout or pattern can be a random arrangement of depressions 16 and/or interstitial regions 22. The pattern may include spots, pads, wells, posts, stripes, swirls, lines, triangles, rectangles, circles, arcs, checks, plaids, diagonals, arrows, squares, and/or cross-hatches. In an example, the depressions 16 are wells, as shown in FIG. 2C.

The layout or pattern may be characterized with respect to the density of the depressions 16 (i.e., number of depressions 16) in a defined area. For example, the depressions 16 may be present at a density of approximately 2 million per $mm^2$. The density may be tuned to different densities including, for example, a density of at least about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more. Alternatively or additionally, the density may be tuned to be no more than about 50 million per $mm^2$, about 10 million per $mm^2$ about 5 million per $mm^2$, about 2 million per $mm^2$, about 1 million per $mm^2$, about 0.1 million per $mm^2$, about 1,000 per $mm^2$, about 100 per $mm^2$, or less. It is to be further understood that the density of depressions 16 in the cured, patterned resin' 14 can be between one of the lower values and one of the upper values selected from the ranges above. As examples, a high density array may be characterized as having depressions 16 separated by less than about 100 nm, a medium density array may be characterized as having depressions 16 separated by about 400 nm to about 1 µm, and a low density array may be characterized as having depressions 16 separated by greater than about 1 µm. While example densities have been provided, it is to be understood that substrates with any suitable densities may be used.

The layout or pattern of the depressions 16 may also or alternatively be characterized in terms of the average pitch, i.e., the spacing from the center of the depression 16 to the center of an adjacent depression 16 (center-to-center spacing) or from the edge of one depression 16 to the edge of an adjacent depression 16 (edge-to-edge spacing). The pattern can be regular, such that the coefficient of variation around the average pitch is small, or the pattern can be non-regular in which case the coefficient of variation can be relatively large. In either case, the average pitch can be, for example, at least about 10 nm, about 0.1 µm, about 0.5 µm, about 1 µm, about 5 µm, about 10 µm, about 100 µm, or more. Alternatively or additionally, the average pitch can be, for example, at most about 100 µm, about 10 µm, about 5 µm, about 1 µm, about 0.5 µm, about 0.1 µm, or less. The average pitch for a particular pattern of depressions 16 can be between one of the lower values and one of the upper values selected from the ranges above. In an example, the depressions 16 have a pitch (center-to-center spacing) of about 1.5 µm. While example average pitch values have been provided, it is to be understood that other average pitch values may be used.

In the example shown in FIGS. 2A through 2E, the depressions 16 are wells, and thus the cured, patterned resin 14' includes an array of wells in a surface thereof. The wells may be micro wells or nanowells. The size of each well may be characterized by its volume, well opening area, depth, and/or diameter.

Each well can have any volume that is capable of confining a liquid. The minimum or maximum volume can be selected, for example, to accommodate the throughput (e.g., multiplexity), resolution, analyte composition, or analyte reactivity expected for downstream uses of the flow cell. For example, the volume can be at least about $1\times10^{-3}$ μm$^3$, about $1\times10^{-2}$ μm$^3$, about 0.1 μm$^3$, about 1 μm$^3$, about 10 μm$^3$, about 100 μm$^3$, or more. Alternatively or additionally, the volume can be at most about $1\times10^4$ μm$^3$, about $1\times10^3$ μm$^3$, about 100 μm$^3$, about 10 μm$^3$, about 1 μm$^3$, about 0.1 μm$^3$, or less. It is to be understood that the polymer coating 18 can fill all or part of the volume of a well.

The area occupied by each well opening on a surface can be selected based upon similar criteria as those set forth above for well volume. For example, the area for each well opening on a surface can be at least about $1\times10^{-3}$ μm$^2$, about $1\times10^{-2}$ μm$^2$, about 0.1 μm$^2$, about 1 μm$^2$, about 10 μm$^2$, about 100 μm$^2$, or more. Alternatively or additionally, the area can be at most about $1\times10^3$ μm$^2$, about 100 μm$^2$, about 10 μm$^2$, about 1 μm$^2$, about 0.1 μm$^2$, about $1\times10^{-2}$ μm$^2$, or less. The area occupied by each well opening can be greater than, less than or between the values specified above.

The depth of each well can be at least about 0.1 μm, about 1 μm, about 10 μm, about 100 μm, or more. Alternatively or additionally, the depth can be at most about $1\times10^3$ μm, about 100 μm, about 10 μm, about 1 μm, about 0.1 μm, or less. The depth of each well can be greater than, less than or between the values specified above.

In some instances, the diameter of each well can be at least about 50 nm, about 0.1 μm, about 0.5 μm, about 1 μm, about 10 μm, about 100 μm, or more. Alternatively or additionally, the diameter can be at most about $1\times10^3$ μm, about 100 μm, about 10 μm, about 1 μm, about 0.5 μm, about 0.1 μm, or less (e.g., about 50 nm). The diameter of each well can be greater than, less than or between the values specified above.

As shown between FIGS. 2C and 2D, after the resin composition 14 is patterned and cured, the cured, patterned resin 14' may be treated to prepare the surface for application of a polymer coating 18.

In an example, the cured, patterned resin 14' may be exposed to silanization, which attaches a silane or the silane derivative to the cured, patterned resin 14'. Silanization introduces the silane or the silane derivative across the surface, including in the depressions 16 (e.g., on the bottom surface and along the side walls) and on the interstitial regions 22.

Silanization may be accomplished using any silane or silane derivative. The selection of the silane or silane derivative may depend, in part, upon the functionalized molecule that is to be used to form the polymer coating 18 (shown in FIG. 2D), as it may be desirable to form a covalent bond between the silane or silane derivative and the polymer coating 18. The method used to attach the silane or silane derivative to the cured, patterned resin 14' may vary depending upon the silane or silane derivative that is being used. Several examples are set forth herein.

In an example, the silane or silane derivative is (3-aminopropyl)triethoxysilane (APTES) or 3-aminopropyl)trimethoxysilane (APTMS) (i.e., X—R$^B$—Si(OR$^C$)$_3$, wherein X is amino, R$^B$ is —(CH$_2$)$_3$—, and R$^C$ is ethyl or methyl). In this example, the substrate 12 surface may be pre-treated with the (3-aminopropyl)triethoxysilane (APTES) or 3-aminopropyl)trimethoxysilane (APTMS) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 J/cm$^2$ to 30 J/cm$^2$ of energy generates an active nitrene species, which can readily undergo a variety of insertion reactions with PAZAM (e.g., one example of the functionalized molecule used to form the polymer coating 18).

Other silanization methods may also be used. Examples of suitable silanization methods include vapor deposition (e.g., a YES method), spin coating, or other deposition methods. Some examples of methods and materials that may be used to silanize cured, patterned resin 14' are described herein, although it is to be understood that other methods and materials may be used.

In an example utilizing the YES CVD oven, the cured, patterned resin 14' on the substrate 12 is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative (e.g., liquid norbornene silane) may be deposited inside a glass vial and placed inside a glass vacuum desiccator with a patterned substrate 12. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivatives, such as those silane or silane derivative including a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo[4.2.1]non-1 (8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl]trimethoxysilane. As other examples, these methods may be used when the silane or silane derivative includes a cycloalkyne unsaturated moiety, such as cyclooctyne, a cyclooctyne derivative, or bicyclononynes (e.g., bicyclo[6.1.0]non-4-yne or derivatives thereof, bicyclo[6.1.0]non-2-yne, or bicyclo[6.1.0]non-3-yne). These cycloalkynes can be substituted with any of the R groups described herein.

The attachment of the silane or silane derivative forms a pre-treated (e.g., silanized) cured, patterned resin 14', which includes silanized depressions and silanized interstitial regions.

In other examples, the cured, patterned resin 14' may not be exposed to silanization. Rather, the cured, patterned resin 14' may be exposed to plasma ashing, and then the polymer coating 18 may be directly spin coated (or otherwise deposited) on the plasma ashed cured, patterned resin 14'. In this example, plasma ashing may generate surface-activating agent(s) (e.g., hydroxyl (C—OH or Si—OH) and/or carboxyl groups) that can adhere the polymer coating 18 to the cured, patterned resin 14'. In these examples, the polymer coating 18 is selected so that it reacts with the surface groups generated by plasma ashing.

In still other examples, the cured, patterned resin 14' may include unreacted epoxy groups (e.g., when the epoxy resin matrix is used with the free radical curable resin matrix); and thus may not be exposed to silanization because the unreacted epoxy groups can react directly with amino functional groups of the polymer coating 18. In this example, plasma ashing may be performed, e.g., if it is desirable to clean the surface of potential contaminants.

The polymer coating 18 may then be applied to the pre-treated cured, patterned resin 14' (as shown between FIGS. 2C and 2C). The polymer coating 18 may be a semi-rigid polymeric material that is permeable to liquids and gases and that is tethered to the cured, patterned resin 14'.

An example of the polymer coating 18 includes an acrylamide copolymer, such as poly(N-(5-azidoacetamidyl-pentyl)acrylamide-co-acrylamide, PAZAM. PAZAM and some other forms of the acrylamide copolymer are represented by the following structure (I):

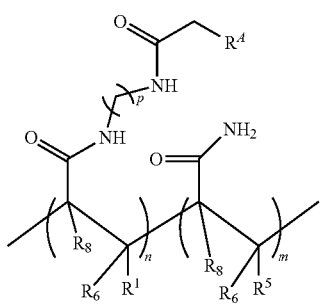

wherein:

$R^1$ is H or optionally substituted alkyl;

$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;

$R^5$, $R_6$, and $R_8$ are each independently selected from the group consisting of H and optionally substituted alkyl;

each of the —$(CH_2)_p$— can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of the PAZAM may range from about 10 kDa to about 1500 kDa, or may be, in a specific example, about 312 kDa.

In some examples, PAZAM is a linear polymer. In some other examples, PAZAM is a lightly cross-linked polymer.

In other examples, the polymer coating 18 may be a variation of the structure (I). In one example, the acrylamide unit may be replaced with N,N-dimethylacrylamide

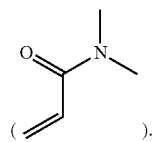

In this example, the acrylamide unit in structure (I) may be replaced with

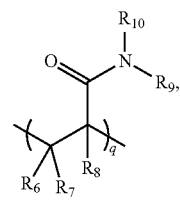

where $R_6$, $R_7$, and $R_8$ are each H, and $R_9$ and $R_{10}$ are each a methyl group (instead of H as is the case with the acrylamide). In this example, q may be an integer in the range of 1 to 100,000. In another example, the N,N-dimethylacrylamide may be used in addition to the acrylamide unit. In this example, structure (I) may include

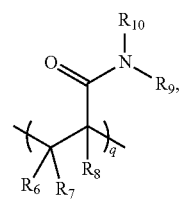

in addition to the recurring "n" and "m" features, where $R_6$, $R_7$, and $R_8$ are each H, and $R_9$ and $R_{10}$ are each a methyl group. In this example, q may be an integer in the range of 1 to 100,000.

As another example polymer, the recurring "n" feature in structure (I) may be replaced with a monomer including a heterocyclic azido group having structure (II):

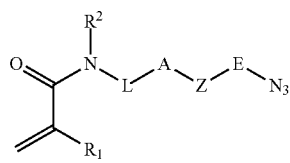

wherein $R^1$ is H or C1-C4 alkyl; $R_2$ is H or C1-C4 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or C1-C4 alkyl attached to the N; and Z is a nitrogen containing heterocycle. Examples of Z include 5 to 10 ring members present as a single cyclic structure or a fused structure.

As still another example, the polymer may include a recurring unit of each of structure (III) and (IV):

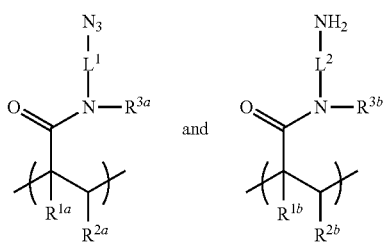

wherein each of $R^{1a}$, $R^{2a}$, $R^{1b}$ and $R^{2b}$ is independently selected from hydrogen, optionally substituted alkyl or optionally substituted phenyl; each $R^{3a}$ and $R^{3b}$ is independently selected from hydrogen, optionally substituted alkyl, optionally substituted phenyl, or optionally substituted C7-C14 aralkyl; and each $L^1$ and $L^2$ is independently selected from an optionally substituted alkylene linker or an optionally substituted heteroalkylene linker.

It is to be understood that other functionalized molecules may be used to form the polymer coating 18, as long as they are functionalized to interact with the pre-treated cured, patterned resin 14' and the subsequently applied primer(s) 24. Other examples of suitable molecules for forming the polymer coating 18 include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photocycloaddition reactions. Still other examples of suitable molecules for forming the polymer coating 18 include mixed copolymers of acrylamides and acrylates. Branched polymers, such as star polymers, star-shaped or star-block polymers, dendrimers, and the like may also be used.

The functionalized molecule (e.g., PAZAM) may be deposited on the surface of the pre-treated cured, patterned resin 14' using spin coating, or dipping or dip coating, or flow of the functionalized molecule under positive or negative pressure, or another suitable technique. The functionalized molecule may be present in a mixture. In an example, the mixture includes PAZAM in water or in an ethanol and water mixture.

After being coated, the functionalized molecule may also be exposed to a curing process to form the polymer coating 18 across the entire patterned substrate (i.e., in depression(s) 16 and on interstitial region(s) 22). In an example, curing the functionalized molecule may take place at a temperature ranging from room temperature (e.g., about 25° C.) to about 95° C. for a time ranging from about 1 millisecond to about several days. In another example, the time may range from 10 seconds to at least 24 hours. In still another example, the time may range from about 5 minutes to about 2 hours.

The attachment of the polymer coating 18 to the pre-treated depressions and interstitial regions may be through covalent bonding. The covalent linking of the polymer coating 18 to the silanized or plasma ashed depressions is helpful for maintaining the polymer coating 18 in the depressions 16 throughout the lifetime of the ultimately formed flow cell during a variety of uses. The following are some examples of reactions that can take place between the silane or silane derivative and the polymer coating 18.

When the silane or silane derivative includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; undergo a cycloaddition reaction with a hydrazone group attached to PAZAM; undergo a photo-click reaction with a tetrazole group attached to PAZAM; or undergo a cycloaddition with a nitrile oxide group attached to PAZAM.

When the silane or silane derivative includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative includes a bicyclononyne as the unsaturated moiety, the bicyclononyne can undergo similar SPAAC alkyne cycloaddition with azides or nitrile oxides attached to PAZAM due to the strain in the bicyclic ring system.

To form the polymer coating 18 in the depression(s) 16 and not on the interstitial region(s) 22 of the cured, patterned resin 14', the polymer coating 18 may be polished off of the interstitial regions 22. The polishing process may be performed with a gentle chemical slurry (including, e.g., an abrasive, a buffer, a chelating agent, a surfactant, and/or a dispersant) which can remove the polymer coating 18 from the interstitial regions 22 without deleteriously affecting the underlying cured, patterned resin 14' and/or substrate 12 at those regions. Alternatively, polishing may be performed with a solution that does not include the abrasive particles. The chemical slurry may be used in a chemical mechanical polishing system. In this example, polishing head(s)/pad(s) or other polishing tool(s) is/are capable of polishing the polymer coating 18 from the interstitial regions 22 while leaving the polymer coating 18 in the depressions 16 and leaving the underlying cured, patterned resin 14' at least substantially intact. As an example, the polishing head may be a Strasbaugh ViPRR II polishing head. In another example, polishing may be performed with a polishing pad and a solution without any abrasive. For example, the polish pad may be utilized with a solution free of the abrasive particle (e.g., a solution that does not include abrasive particles).

FIG. 2D depicts the flow cell precursor 10 after the polymer layer 18 has been applied to the depressions 16. The flow cell precursor 10 may be exposed to a cleaning process. This process may utilize a water bath and sonication. The water bath may be maintained at a relatively low temperature ranging from about 22° C. to about 30° C. The silanized, coated, and polished patterned substrate may also be spin dried, or dried via another suitable technique.

As shown between FIGS. 2D and 2E, a grafting process is performed in order to graft a primer 24 to the polymer coating 18 in the depression(s) 16. The primer 24 may be any forward amplification primer or reverse amplification primer that includes an alkyne functional group, or another terminated primer. Other examples of terminated primers that may be used include a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, a phosphoramidite terminated primer, and a triazolinedione terminated primer. A mixture of primers may also be used. Specific examples of suitable primers include P5 and/or P7 primers, which are used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, ISEQ™, GENOME ANALYZER™, and other instrument platforms.

In an example, grafting may be accomplished by flow through deposition (e.g., using a temporarily bound lid), dunk coating, spray coating, puddle dispensing, or by another suitable method that will attach the primer(s) 24 to the polymer coating 18. Each of these example techniques may utilize a primer solution or mixture, which may include the primer(s), water, a buffer, and a catalyst.

Dunk coating may involve submerging the flow cell precursor 10 (shown in FIG. 2D) into a series of temperature controlled baths. The baths may also be flow controlled and/or covered with a nitrogen blanket. The baths may include the primer solution or mixture. Throughout the various baths, the primer(s) 24 will attach to the primer-grafting functional group(s) of the polymer coating 18 in at least some of the depression(s) 16. In an example, the flow cell precursor 10 will be introduced into a first bath including the primer solution or mixture where a reaction takes place to attach the primer(s) 24, and then moved to additional baths for washing. Movement from bath to bath may involve a robotic arm or may be performed manually. A drying system may also be used in dunk coating.

Spray coating may be accomplished by spraying the primer solution or mixture directly onto the flow cell precursor 10. The spray coated wafer may be incubated for a time ranging from about 4 minutes to about 60 minutes at a temperature ranging from about 0° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the flow cell precursor 10. The applied primer solution or mixture may be applied to or spread across the entire surface of the flow cell precursor 10. The primer coated flow cell precursor 10 may be incubated for a time ranging from about 2 minutes to about 60 minutes at a temperature ranging from about 0° C. to about 80° C. After incubation, the primer solution or mixture may be diluted and removed using, for example, the spin coater.

FIG. 2F illustrates an example of the flow cell 10' after primer grafting. While a single type of primer 24 is shown, it is to be understood that two or more different primers 24 may be attached.

The examples shown in FIGS. 2E and 2F are examples of the flow cell 10' without a lid bonded thereto. While not shown, the flow cells 10' may have the lid bonded to at least a portion of the interstitial region 22. The lid may be bonded before or after primer 24 grafting. When the lid is performed prior to primer 24 grafting, it is to be understood that a flow through process may be used for grafting. In the flow through process, the primer solution or mixture may be introduced into a flow channel(s) (defined between the lid and the interstitial region 22) through respective input port(s) (not shown), may be maintained in the flow channel(s) for a time sufficient (i.e., an incubation period) for the primer(s) 24 to attach to the polymer coating 18 in one or more of the depressions 16 and then may be removed from respective output port(s) (not shown). After primer 24 attachment, the additional fluid(s) may be directed through the flow channel(s) to wash the now functionalized depressions and the flow channel(s).

The lid may be positioned on the interstitial region 22 so that it defines a single flow channel or multiple, fluidically separated flow channels.

The lid may be any material that is transparent to an excitation light that is directed toward the depression(s) 16. As examples, the lid may be glass (e.g., Corning Eagle XG (CEXG), borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

In some examples, the lid may be integrally formed with sidewall(s) that correspond with the shape of the portion of the interstitial region 22 to which it will be bonded. For example, a recess may be etched into a transparent block to form a substantially planar (e.g., top) portion and sidewall(s) extending from the substantially planar portion. When the etched block is mounted to the interstitial region 22, the recess may become the flow channel.

In other examples, the sidewall(s) and the lid may be separate components that are coupled to each other. For example, the lid may be a substantially rectangular block having an at least substantially planar exterior surface and an at least substantially planar interior surface that defines a portion (e.g., a top portion) of the flow channel (once bonded to the portion of the interstitial region 22). The block may be mounted onto (e.g., bonded to) the sidewall(s), which are bonded to the portion of the interstitial region 22 and form sidewall(s) of the flow channel. In this example, the sidewall(s) may include any of the materials set forth herein for the spacer layer (described below).

The lid may be bonded using any suitable technique, such as laser bonding, diffusion bonding, anodic bonding, eutectic bonding, plasma activation bonding, glass frit bonding, or others methods known in the art. In an example, a spacer layer may be used to bond the lid to the portion of the interstitial region 22. The spacer layer may be any material that will seal at least some of the interstitial regions 22 and the lid together.

In one example, the spacer layer may be a radiation-absorbing material that absorbs radiation at a wavelength that is transmitted by the lid and/or the cured, patterned resin 14'. The absorbed energy, in turn, forms the bond between the spacer layer and the lid and between the spacer layer and the cured, patterned resin 14'. An example of this radiation-absorbing material is black KAPTON® (polyimide containing carbon black) from DuPont (USA), which absorbs at about 1064 nm. It is to be understood that polyimide could be used without the addition of carbon black, except that the wavelength would have to be altered to one that is significantly absorbed by the natural polyimide material (e.g., 480 nm). As another example, polyimide CEN JP can be bonded when irradiated with light at 532 nm. When the spacer layer is the radiation-absorbing material, the spacer layer may be positioned at an interface between the lid and the portion of the interstitial region 22 so that the spacer layer contacts the desired bonding region. Compression may be applied (e.g., approximately 100 PSI of pressure) while laser energy at a suitable wavelength is applied to the interface (i.e., the radiation-absorbing material is irradiated). The laser energy may be applied to the interface both from the top and from the bottom in order to achieve suitable bonding.

In another example, the spacer layer may include a radiation-absorbing material in contact therewith. The radiation-absorbing material may be applied at the interface between the spacer layer and the lid as well as at the interface between the spacer layer and the portion of the interstitial region 22. As an example, the spacer layer may be polyimide and the separate radiation-absorbing material may be carbon black. In this example, the separate radiation-absorbing material absorbs the laser energy that forms the bonds between the spacer layer and the lid and between the spacer layer and the portion of the interstitial region 22. In this example, compression may be applied at the respective interfaces while laser energy at a suitable wavelength is applied to the interfaces (i.e., the radiation-absorbing material is irradiated).

The flow cells 10' disclosed herein may be used in a variety of sequencing approaches or technologies, including techniques often referred to as sequencing-by-synthesis (SBS), cyclic-array sequencing, sequencing-by-ligation, pyrosequencing, and so forth. With any of these techniques, since the polymer coating 18 and attached primer(s) 24 are present in the depressions 16 and not on the interstitial regions 22, amplification will be confined to the depressions.

As one example, a sequencing by synthesis (SBS) reaction may be run on a system such as the HISEQ™, HISEQX™, MISEQ™, MISEQDX™, MINISEQ™, ISEQ™, NOVASEQ™, NEXTSEQDX™, or NEXTSEQ™ sequencer systems from Illumina (San Diego, Calif.). In SBS, extension of a nucleic acid primer (e.g., a sequencing primer) along a nucleic acid template (i.e., the sequencing template) is monitored to determine the sequence of nucleotides in the template. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the sequencing primer (thereby extending the sequencing primer) in a template dependent fashion such that detection of the order and type of nucleotides added to the sequencing primer can be used to determine the sequence of the template.

Prior to sequencing, amplification primers 24 can be exposed to a sequencing library, which is amplified using any suitable method, such as cluster generation.

In one example of cluster generation, the library fragments are copied from the hybridized primers 24 by 3' extension using a high-fidelity DNA polymerase. The original library fragments are denatured, leaving the copies immobilized. Isothermal bridge amplification may be used to amplify the immobilized copies. For example, the copied templates loop over to hybridize to an adjacent, complementary primer 24, and a polymerase copies the copied templates to form double stranded bridges, which are denatured to form two single stranded strands. These two strands loop over and hybridize to adjacent, complementary primers 24 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. It is to be understood that clustering results in the formation of several template strands.

To initiate a first SBS cycle, one or more labeled nucleotides, DNA polymerase, etc., may be delivered into/through the flow channel, etc., where sequencing primer extension causes a labeled nucleotide to be incorporated to the template strands. This incorporation can be detected through an imaging event. During an imaging event, an illumination system (not shown) may provide an excitation light to the functionalized depressions. During the imaging event, any emissions (if any) from the cured, patterned resin 14' resulting from exposure to blue and/or green excitation wavelengths may be i) non-detected because they are below a threshold limit of detection, or ii) distinguished as noise due to the low autofluorescence of the cured, patterned resin 14'. As such, the cured, patterned resin 14' disclosed herein is essentially invisible to the detector.

In some examples, the nucleotides can further include a reversible termination property that terminates further primer extension once a nucleotide has been added to the sequencing primer. For example, a nucleotide analog having a reversible terminator moiety can be added to the sequencing primer such that subsequent extension cannot occur until a deblocking agent is delivered to remove the moiety. Thus, for examples that use reversible termination, a deblocking reagent can be delivered to the flow channel, etc. (before or after detection occurs).

Wash(es) may take place between the various fluid delivery steps. The SBS cycle can then be repeated n times to extend the sequencing primer by n nucleotides, thereby detecting a sequence of length n.

While SBS has been described in detail, it is to be understood that the flow cells described herein may be utilized with other sequencing protocol, for genotyping, or in other chemical and/or biological applications. Paired-end sequencing facilitates detection of genomic rearrangements and repetitive sequence elements, as well as gene fusions and novel transcripts. In another example, the flow cells disclosed herein may be used for on-cell library generation.

While the example described in FIGS. 1 and 2A through 2F illustrate the use of the resin composition in the formation of a flow cell, it is to be understood that the resin composition may be used in other applications where low autofluorescence is desired. As one example, the resin composition 14, 14' may be used in any optically-based SBS technique. As other examples, the resin composition 14, 14' may be used in planar waveguides, in complementary metal-oxide semiconductors (CMOS), etc.

To further illustrate the present disclosure, two examples and a prophetic example are given herein. It is to be understood that these examples and prophetic example are provided for illustrative purposes and are not to be construed as limiting the scope of the present disclosure.

EXAMPLES

Example 1

Six examples of the resin composition were prepared. Each example included a different free radical curable resin matrix, which included 1,3-bis(3-methacryloxypropyl) tetramethyldisiloxane, methacryloxypropyl-terminated polydimethylsiloxane, tetramethyl tetrakis[3-acryloxypropyl]cyclotetrasiloxane, methacryl polyhedral oligomeric silsesquioxane, acrylo polyhedral oligomeric silsesquioxane, and acryloxypropyl methylsiloxane homopolymer. Each of these free radical curable resin matrices was mixed with a photoinitiator, namely bis(2,4,6-trimethylbenzoyl)-phenylphosphineoxide (commercially available as OMNI-RAD™ 2022, from IGM Resins).

The free radical curable resin matrices and the photoinitiator were mixed with PGMEA solvent, with the concentration of the monomers ranging from about 15 wt % to about 66 wt % and the concentration of the photoinitiator being about 1 wt %.

Each of these resin compositions was deposited by spin coating at 2200 (revolutions per minute) rpm for about 1 minute on a glass substrate. After deposition, the resin compositions were exposed to a softbake for about 2 minutes at about 130° C. to drive off PGMEA. The deposited resin composition was then imprinted using nanoimprint lithography. A working stamp was pressed into the deposited composition and the resin was exposed to UV curing with an LED UV lamp for about 20 seconds.

SEM images of each of the cured, patterned resins were taken. The images are shown in FIGS. 3A through 3F, respectively, for the cured, patterned resins formed with 1,3-bis(3-methacryloxypropyl) tetramethyldisiloxane, methacryloxypropyl-terminated polydimethylsiloxane, tetramethyl tetrakis[3-acryloxypropyl]cyclotetrasiloxane, methacryl polyhedral oligomeric silsesquioxane, acrylo polyhedral oligomeric silsesquioxane, and acryloxypropyl methylsiloxane homopolymer. These images demonstrate that the resin compositions disclosed herein can be nanoimprinted to form suitable depressions for flow cells or other suitable applications.

Example 2

An example resin composition was prepared including about 17 wt % of acrylo polyhedral oligomeric silsesquioxane (acrylo-POSS—as the free radical curable resin matrix), about 1 wt % of bis(2,4,6-trimethylbenzoyl)-phenylphosphineoxide (as the free radical photoinitiator), and propylene glycol monomethyl ether acetate (PGMEA—a solvent). The solvent made up the balance (about 82 wt %) of the composition.

A comparative resin composition was prepared including about 4 wt % of glycidyl functionalized POSS and about 13 wt % of epoxycyclohexyl ethyl functionalized POSS (as an epoxy resin matrix), about 1.2 wt % total of a photoinitiator/photoacid generator combination of thioxanth-9-one (ITX) (present at about 0.34 wt %)/TEGO® PC 1467 (Evonik Industries) (present at about 0.85 wt %), about 1.4 wt % polyacrylate (BYK®-350), and a solvent (PGMEA). The solvent made up the balance (about 80 wt %) of the composition.

Each of the comparative example resin composition example resin composition was deposited on a glass substrate by spin coating at 2200 (revolutions per minute) rpm for about 1 minute.

After deposition of the example and comparative example resin compositions, the example and comparative resin compositions were exposed to a softbake for about 2 minutes at about 120° C. to drive off PGMEA. Then, the resins were UV cured with an LED UV lamp for about 20 seconds. The comparative example resin was hardbaked at 250° C. for about 10 minutes after the UV curing. The example resin was not hardbaked.

Then the cured example and the cured comparative example were exposed to excitation wavelengths using a spectrometer based tool. The tool excitation source was a 445 nm (blue) laser. The laser spot size is about 200 µm. The laser beam passed through a filter to filter out some higher wavelength lines and then passed through the samples. Transparent samples (of the cured example and the cured comparative example) were used for the measurement. In line with the laser beam on the other side of the sample was an Ocean Optics spectrometer that was fiber-optically coupled. The incident laser power can be tuned by adjusting the drive current or adding attenuating filters in front of the laser beam. For the measurements shown in the graph of FIG. 4, a laser power of 3 mW was used.

Figure 4:
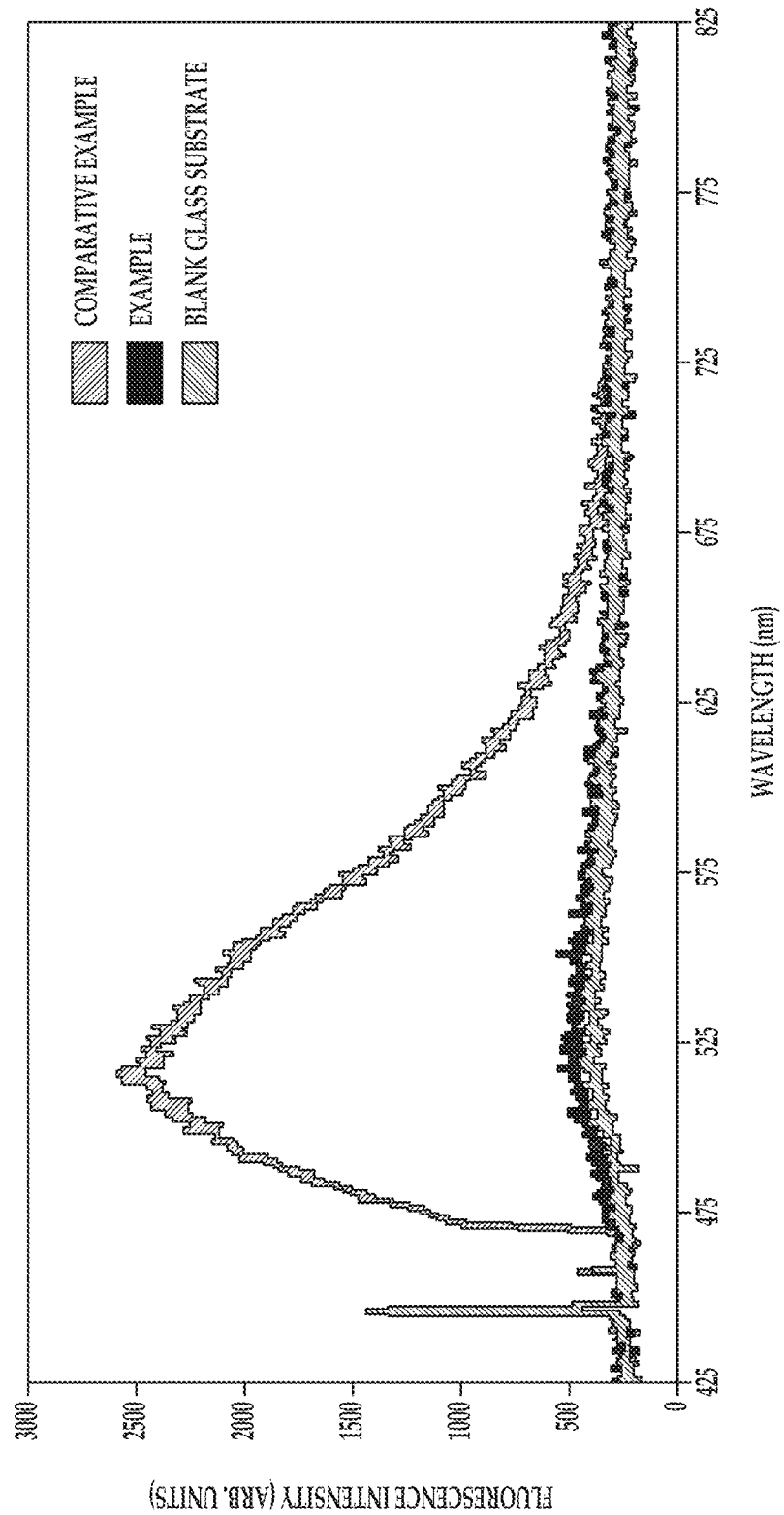
FIG. 4 is a graph illustrating fluorescence intensity (in arbitrary units) versus wavelength (in nanometers (nm)) for a comparative example resin, an example resin, and a blank glass substrate.

As can be seen from the graph of FIG. 4, the fluorescence intensity (in arbitrary units (AU)) of the comparative example in the blue excitation wavelengths is as high as 2,500 AU, and in the green excitation wavelengths ranges from about 2,000 AU to about 2,400 AU. In contrast, the fluorescence intensity of the example in the blue and green excitation wavelengths is generally below about 500 AU, and does not appear to be significantly higher than the fluorescence intensity of the blank glass substrate.

Prophetic Example

The intent of this prophetic example is to compare two formulations in a hypothetical example.

An example resin composition includes 1,3-bis(3-methacryloxypropyl) tetramethyldisiloxane (as the free radical curable resin matrix) and bis(2,4,6-trimethylbenzoyl)-phenylphosphineoxide (as the free radical photoinitiator) in PGMEA.

A comparative resin composition includes glycidyl functionalized POSS and epoxycyclohexyl ethyl functionalized POSS (as an epoxy resin matrix), a photoinitiator/photoacid generator combination of thioxanth-9-one (ITX) and TEGO® PC 1467 (Evonik Industries) in PGMEA.

The comparative example composition is deposited in the first two lanes (1 and 2) of a glass or silicon flow cell, and the example composition is deposited in the last two lanes (4 and 5) of the glass or silicon flow cell.

After deposition of the example and comparative example resin compositions, the resins are cured.

Figure 5A:
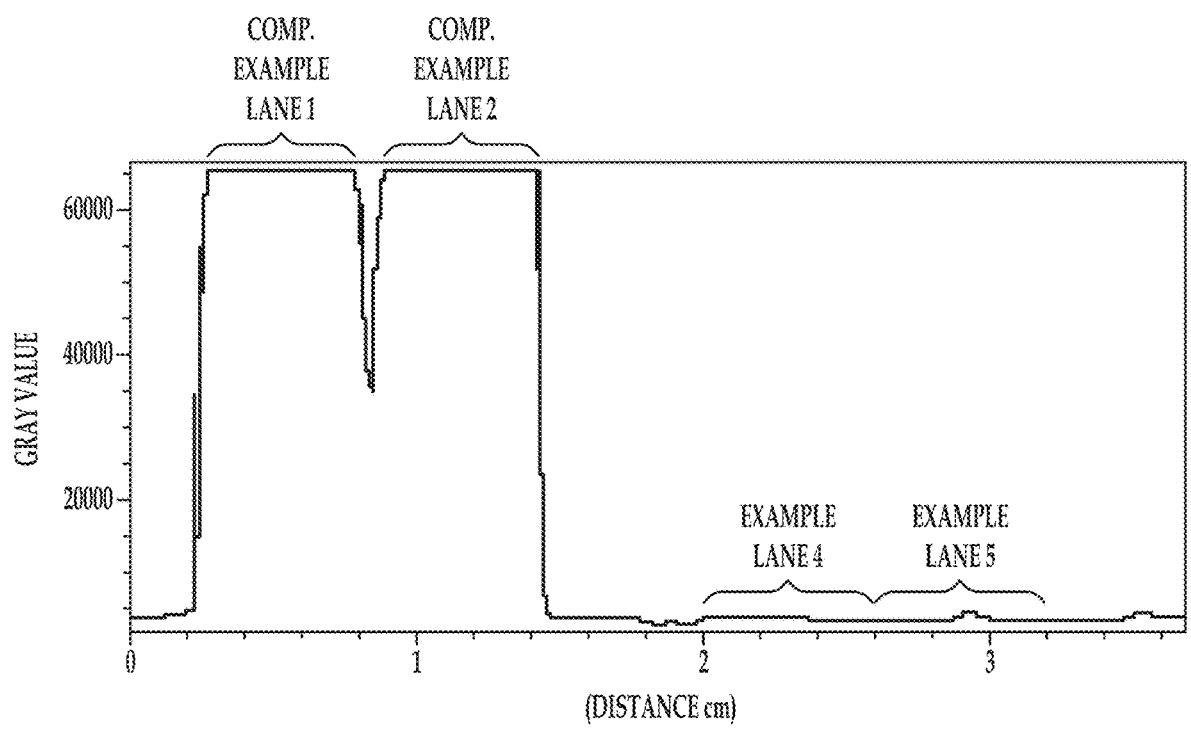
FIGS. 5A and 5B are graphs illustrating proposed autofluorescence results for a prophetic example resin composition and a prophetic comparative example resin composition.
Figure 5B:
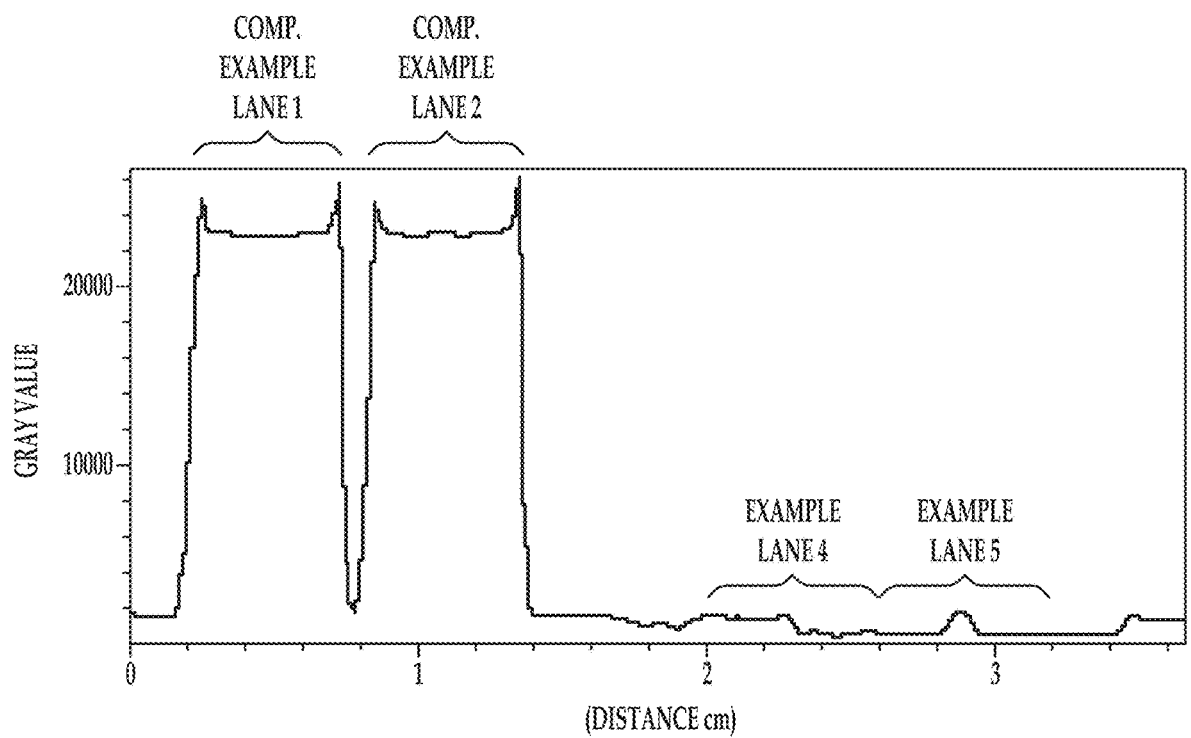

Each of the cured example and the cured comparative example is respectively exposed to blue excitation wavelengths and green excitation wavelengths using an Amersham TYPHOON™ autofluorescence tool. It is believed that the autofluorescence results for the comparative example will be much higher than for the example. FIGS. 5A and 5B are graphs illustrating proposed results for the autofluorescence of the cured example and of the cured comparative example when exposed, respectively, to blue excitation wavelengths (FIG. 5A) and green excitation wavelengths (FIG. 5B). In these figures, the grey values represent the autofluorescence and the distance in cm at which the lanes are located on the flow cell.

This prophetic example compares a hypothetical acrylate based formulation with a hypothetical epoxy resin based formulation, and sets forth proposed autofluorescence results for each of the hypothetical formulations to illustrate that the combination of the free radical curable resin matrix including an acrylate and a siloxane and the free radical photoinitiator may lead to lower autofluorescence.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such values or sub-ranges were explicitly recited. For example, a range from about 380 nm to about 480 nm, should be interpreted to include not only the explicitly recited limits of from about 380 nm to about 480 nm, but also to include individual values, such as about 408 nm, about 445.5 nm, etc., and sub-ranges, such as from about 425 nm to about 475 nm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A resin composition, comprising:
a free radical curable resin matrix including an acrylate and a siloxane, the free radical curable resin matrix being selected from the group consisting of 1,3-bis(3-methacryloxypropyl) tetramethyldisiloxane, tetramethyl tetrakis[3-acryloxypropyl]cyclotetrasiloxane, acryloxypropyl methylsiloxane homopolymer, and combinations thereof;
a free radical photoinitiator, the free radical photoinitiator being phenylbis(2,4,6-trimethylbenzoyl)phosphine oxide;
an epoxy resin matrix; and
a photoacid generator.

2. A flow cell, comprising:
a substrate; and
a cured, patterned resin on the substrate, the cured, patterned resin including depressions separated by interstitial regions, and the cured, patterned resin having been formed from the resin composition of claim 1.

3. The flow cell as defined in claim 2, further comprising:
a polymer coating in the depressions; and
a primer grafted to the polymer coating.

4. A method of making a flow cell, comprising:
depositing the resin composition of claim 1 on a substrate;
nanoimprinting the deposited resin composition using a working stamp; and
curing the deposited resin composition to form a cured, patterned resin.

5. The resin composition as defined in claim 1, wherein a weight % ratio of the epoxy resin matrix to the photoacid generator in the resin composition ranges from about 99.8: 0.2 to about 90:10.

6. The resin composition as defined in claim 1, wherein the epoxy resin matrix is selected from the group consisting of:
i) an epoxy functionalized polyhedral oligomeric silsesquioxane (POSS);

ii) trimethylolpropane triglycidyl ether:

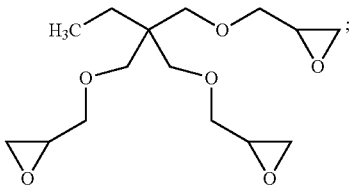 [SMILES: CCC(COCC1CO1)(COCC1CO1)COCC1CO1]

iii) tetrakis(epoxycyclohexyl ethyl)tetramethyl cyclotetrasiloxane:

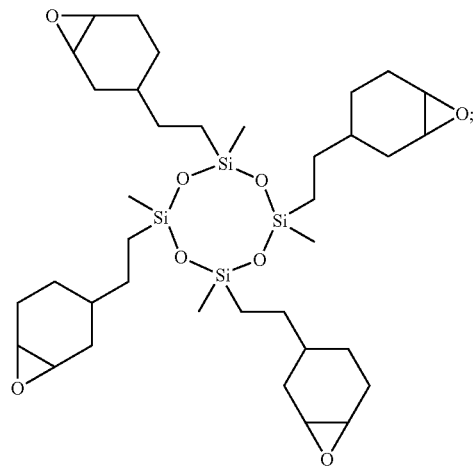 [SMILES: C[Si]1(CCC2CCC3OC3C2)O[Si](C)(CCC2CCC3OC3C2)O[Si](C)(CCC2CCC3OC3C2)O[Si](C)(CCC2CCC3OC3C2)O1]

iv) a copolymer of (epoxycyclohexylethyl)methylsiloxane and dimethylsiloxane:

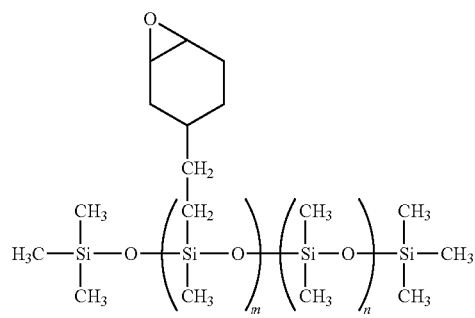

(wherein a ratio of m:n ranges from 8:92 to 10:90);

v) 1,3-bis[2-(3,4-epoxycyclohexyl) ethyl] tetramethyl disiloxane:

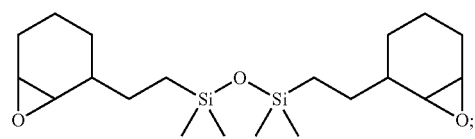 [SMILES: C[Si](C)(CCC1CCCC2OC12)O[Si](C)(C)CCC1CCCC2OC12]

vi) 1,3-bis(glycidoxypropyl)tetramethyl disiloxane:

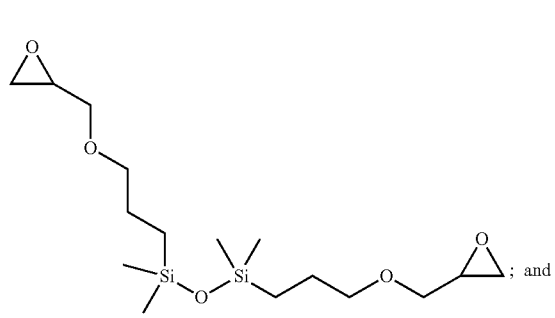 [SMILES: C[Si](C)(CCCOCC1CO1)O[Si](C)(C)CCCOCC1CO1]
; and vii) combinations thereof.

7. The resin composition as defined in claim 1, wherein the photoacid generator is selected from the group consisting of:

i) N-hydroxynaphthalimide triflate:

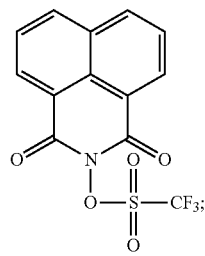 [SMILES: O=C1c2cccc3cccc(c23)C(=O)N1OS(=O)(=O)C(F)(F)F]

ii) triarylsulfonium hexafluorophosphate salts, mixed:

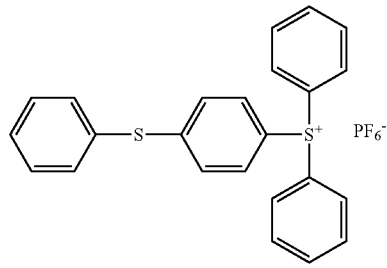

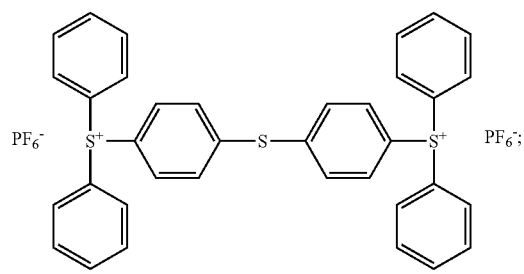

iii) triarylsulfonium hexafluoroantimonate salts, mixed:

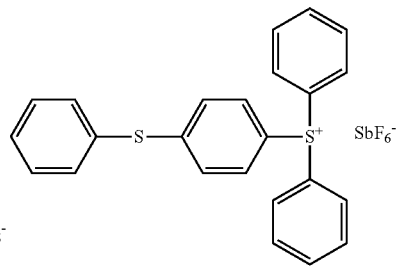

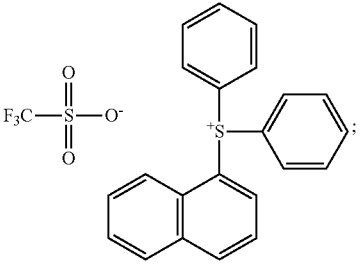 [SMILES: O=S(=O)([O-])C(F)(F)F ; c1ccc([S+](c2ccccc2)c2cccc3ccccc23)cc1]

iv) 1-naphthyl diphenylsulfonium triflate (NDS-TF):

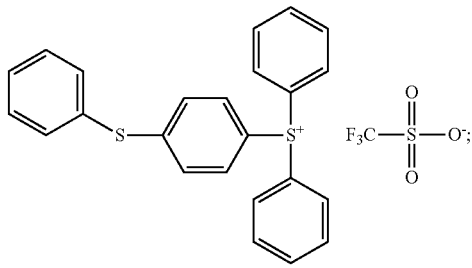

v) (4-phenylthiophenyl)diphenylsulfonium triflate:

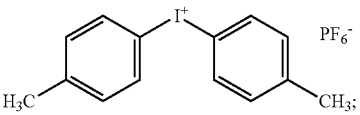

vi) bis-(4-methylphenyl)iodonium hexafluorophosphate:

vii) bis(4-tert-butylphenyl)iodonium hexafluorophosphate:

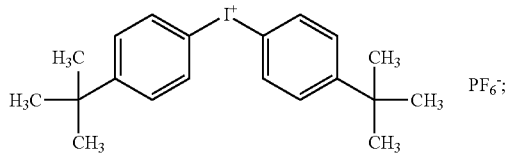 [SMILES: CC(C)(C)c1ccc([I+]c2ccc(C(C)(C)C)cc2)cc1]

viii) (2-methylphenyl)(2,4,6-trimethylphenyl)iodonium triflate:

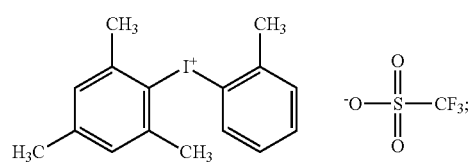

xi) bis(2,4,6-trimethylphenyl)iodonium triflate:

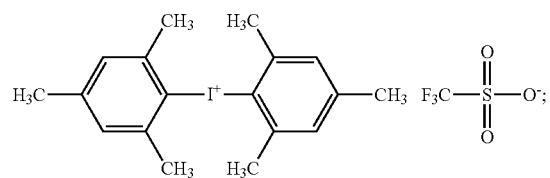

x) bis-(4-dedecylphenyl)iodonium hexafluoroantimonate salt:

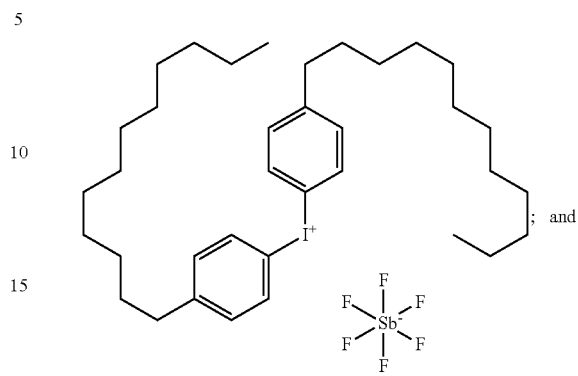

; and xi) combinations thereof.

8. The resin composition as defined in claim 1, further comprising a surfactant selected from the group consisting of a polyethylene sorbitol ester, a polyoxyethylene sorbitol ester, or octylphenol ethoxylate.

9. The resin composition as defined in claim 1, further comprising a solvent selected from the group consisting of propylene glycol monomethyl ether acetate, toluene, dimethyl sulfoxide, and tetrahydrofuran.

* * * * *